(12) United States Patent
Hughes

(10) Patent No.: US 9,101,776 B2
(45) Date of Patent: Aug. 11, 2015

(54) IMPLANTABLE MEDICAL ELECTRICAL LEAD CONNECTOR ASSEMBLIES AND METHODS OF MANUFACTURE

(71) Applicant: Medtronic, Inc., Minneapolis, MN (US)

(72) Inventor: Jonathan A Hughes, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/197,335

(22) Filed: Mar. 5, 2014

(65) Prior Publication Data

US 2015/0165217 A1    Jun. 18, 2015

Related U.S. Application Data

(63) Continuation-in-part of application No. 14/132,211, filed on Dec. 18, 2013.

(51) Int. Cl.
*H01R 24/04* (2006.01)
*A61N 1/375* (2006.01)
*H01R 13/516* (2006.01)
*H01R 43/16* (2006.01)

(52) U.S. Cl.
CPC ............ *A61N 1/3752* (2013.01); *H01R 13/516* (2013.01); *H01R 43/16* (2013.01)

(58) Field of Classification Search
CPC ...................................................... H01R 24/58
USPC ................................................ 439/669, 909
See application file for complete search history.

(56) References Cited

U.S. PATENT DOCUMENTS

| | | | |
|---|---|---|---|
| 5,304,219 A | 4/1994 | Chernoff et al. | |
| 5,376,206 A * | 12/1994 | Maurer et al. | 439/669 |
| 7,108,549 B2 | 9/2006 | Lyu et al. | |
| 7,175,478 B2 * | 2/2007 | Ollivier | 439/669 |
| 7,187,974 B2 | 3/2007 | Haeg et al. | |
| 7,241,180 B1 * | 7/2007 | Rentas Torres | 439/669 |
| 7,274,963 B2 | 9/2007 | Spadgenske | |
| 7,326,083 B2 * | 2/2008 | Mehdizadeh et al. | 439/909 |

(Continued)

FOREIGN PATENT DOCUMENTS

CN    102210901 A    12/2011

OTHER PUBLICATIONS (PCT/US2014/070444) PCT Notification of Transmittal of the International Search Report and the Written Opinion of the International Searching Authority.

*Primary Examiner* — Tho D Ta
(74) *Attorney, Agent, or Firm* — Michael C. Soldner

(57) ABSTRACT

An implantable lead connector assembly includes contact rings, and a bulk of insulation, which includes sealing surfaces and a shank defining a distal end of the bulk. One or more conductor pins extend within the bulk and have distal ends protruding distally therefrom to be exposed alongside the shank; and an inner surface of each contact ring may have a proximal end of a corresponding conductor pin coupled thereto. The sealing surfaces, in conjunction with outer contact surfaces of the contact rings, which are interspersed therebetween, define a uniform outer diameter for the connector assembly. The bulk of insulation may be formed in two parts, wherein a primary bulk is formed around a core and includes circuit-support and shank segments. A secondary bulk, which includes the aforementioned sealing surfaces, is injection molded around the primary bulk, after positioning the contact rings and corresponding conductor pins on the circuit-support segment thereof.

17 Claims, 17 Drawing Sheets

(56) References Cited

U.S. PATENT DOCUMENTS

| | | |
|---|---|---|
| 7,395,116 B2 | 7/2008 | Mehdizadeh et al. |
| 7,551,967 B1 | 6/2009 | Karicherla et al. |
| 7,647,110 B2 | 1/2010 | Hornfeldt et al. |
| 7,648,401 B2 * | 1/2010 | Guenther et al. ............ 439/669 |
| 7,822,476 B2 | 10/2010 | Bartels et al. |
| 8,911,265 B2 * | 12/2014 | Maio et al. ................... 439/669 |
| 2008/0234778 A1 | 9/2008 | Rebentisch |
| 2008/0303728 A1 | 12/2008 | Lee et al. |
| 2011/0065301 A1 | 3/2011 | Boyd et al. |
| 2011/0137414 A1 | 6/2011 | Litzke et al. |
| 2011/0159748 A1 | 6/2011 | Lim et al. |
| 2012/0019260 A1 | 1/2012 | Reddy et al. |
| 2012/0053646 A1 | 3/2012 | Brase et al. |
| 2012/0151765 A1 | 6/2012 | James et al. |
| 2012/0239124 A1 | 9/2012 | Fan et al. |
| 2012/0322317 A1 | 12/2012 | Seeley et al. |

* cited by examiner

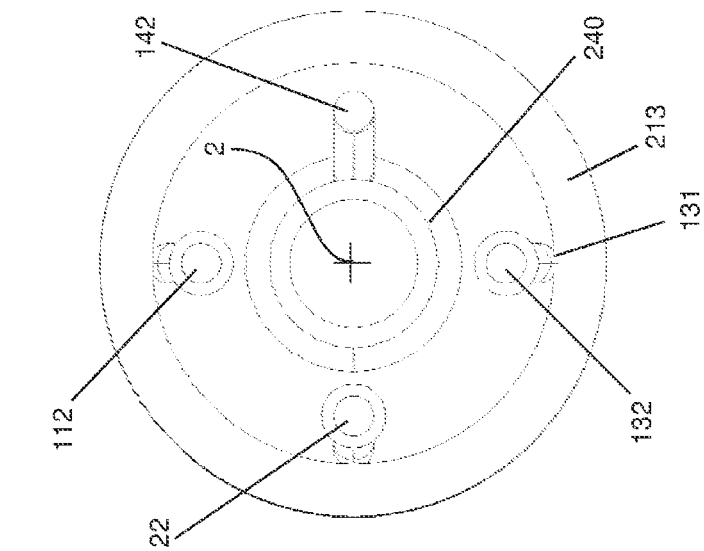
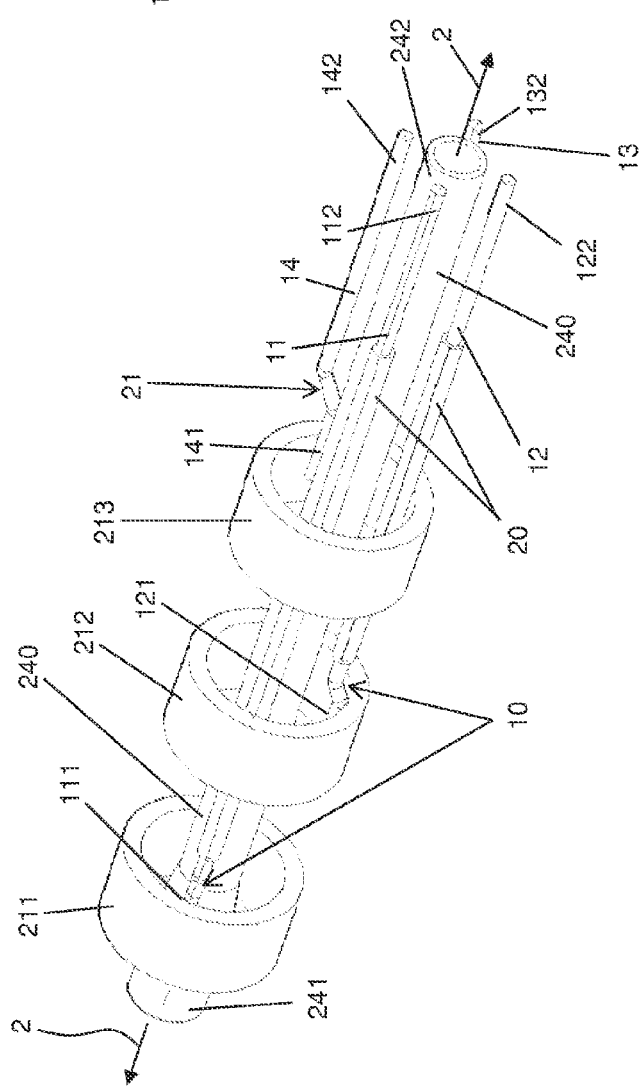

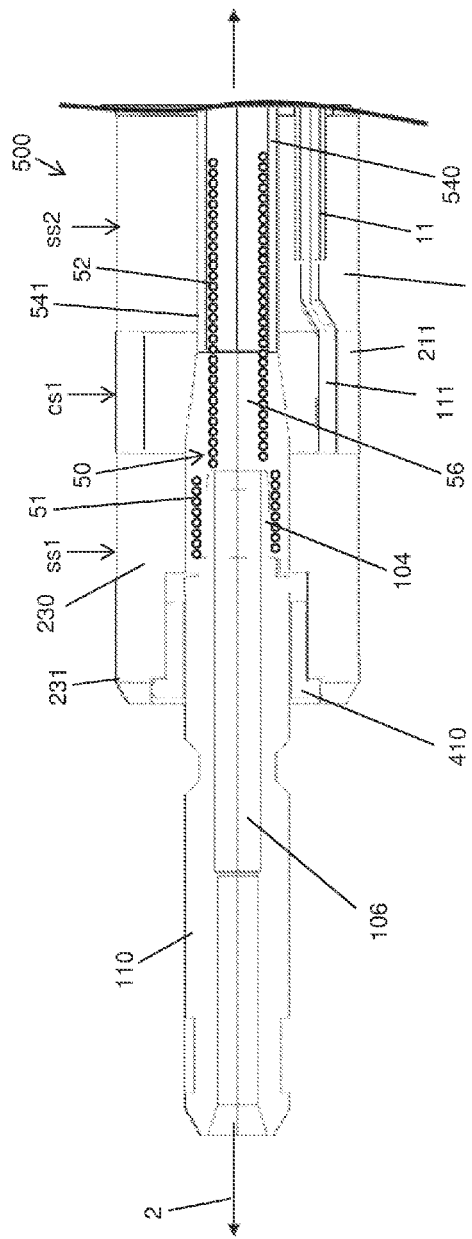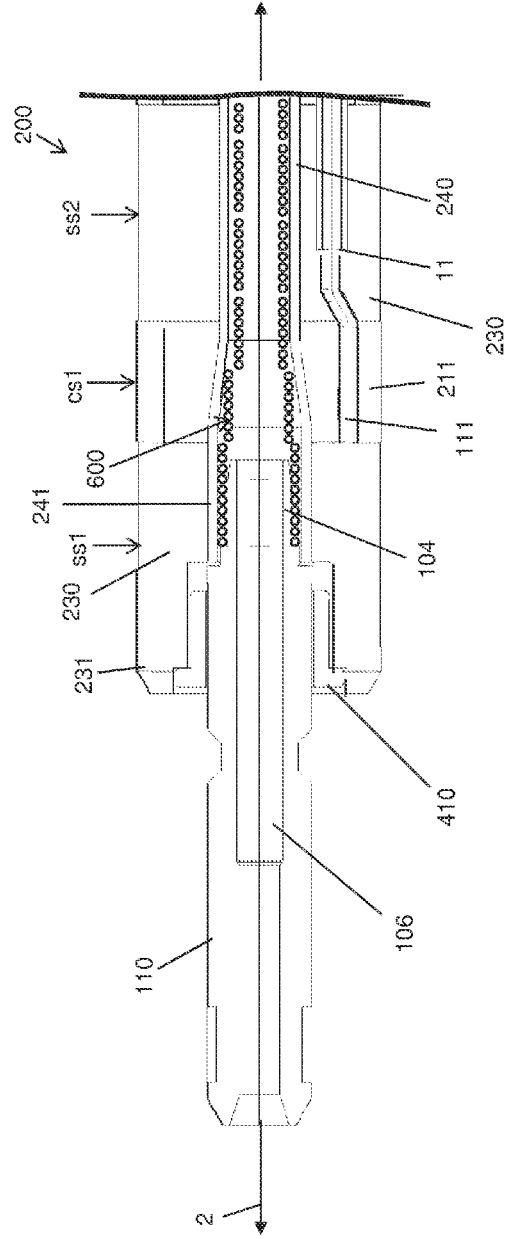

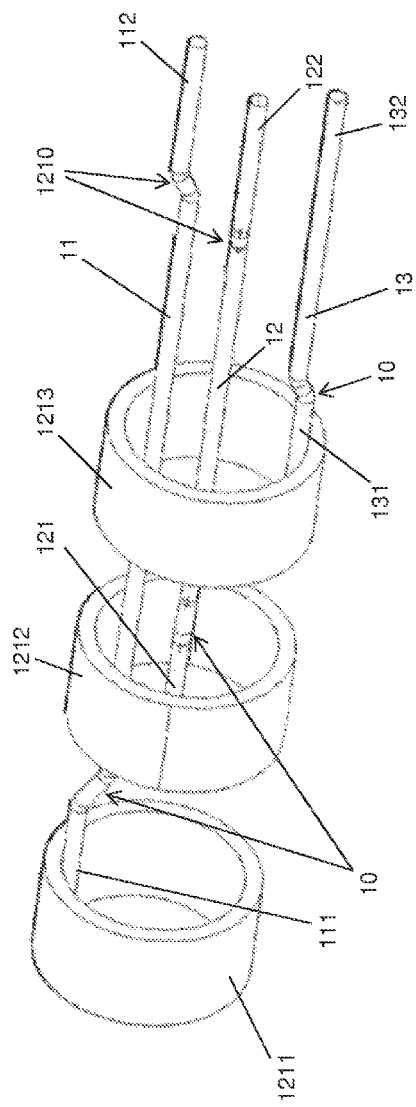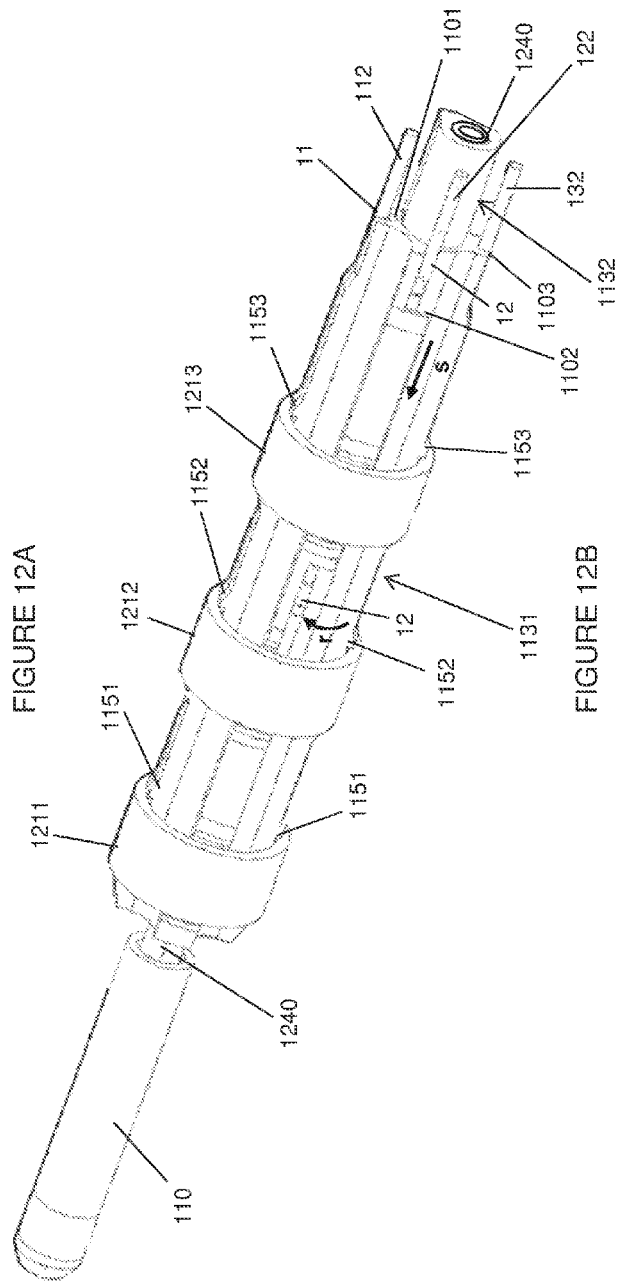

IMPLANTABLE MEDICAL ELECTRICAL LEAD CONNECTOR ASSEMBLIES AND METHODS OF MANUFACTURE

CROSS-REFERENCE TO RELATED APPLICATION

The present application is a continuation-in-part of U.S. patent application Ser. No. 14/132,211, filed on Dec. 18, 2013 and entitled, IMPLANTABLE MEDICAL ELECTRICAL LEAD CONNECTORS, ASSEMBLIES THEREOF, AND METHODS OF MANUFACTURE, which is hereby incorporated by reference, in its entirety.

FIELD OF THE DISCLOSURE

The present disclosure pertains to implantable medical electrical leads, and more particularly to constructions of, and manufacturing methods for lead connectors that are configured to mate with connector receptacles of implantable medical devices.

BACKGROUND

Implantable medical systems, for example, those providing electrical stimulation for cardiac or neurological therapy, often include a pulse generator device and an elongate medical electrical lead that extends from the device to a stimulation site in a body of a patient. Numerous configurations of implantable medical electrical lead connectors have been disclosed over the years, many of which are directed toward compliance with international industry standards; these standards specify essential dimensions and performance requirements to assure compatibility of connection between pulse generator device connector receptacles and lead connectors among a variety of manufacturers. One such standard dictates the form for a four-pole in-line connector of cardiac pacing and defibrillation leads and is commonly known as the IS-4, or in some cases, the DF-4 standard.

FIG. 1 is a schematic with a corresponding chart that describes various configurations of an exemplary implantable medical electrical lead 100. Lead 100 includes a connector 120 in conformance with the aforementioned IS-4 standard. FIG. 1 illustrates connector 120 including a terminal connector pin 110, three contact surfaces cs1, cs2, cs3, and four sealing surfaces ss1, ss2, ss3, and ss4, wherein, according to the IS-4 standard, pin 110 and first contact surface cs1 are low voltage contacts, and second and third contact surfaces cs2, cs3 are high voltage contacts. The IS-4 standard also requires a specific configuration of terminal connector pin 110 and a uniform outer diameter D of connector 120. Those skilled in the art understand that pin 110 and contact surfaces cs1-cs3 are configured to mate with device contacts mounted within a connector receptacle of the device, and sealing surfaces ss1-ss4 are configured to mate with sealing rings, which are interspersed between the contacts within the device connector receptacle, so that an electrical coupling is made between each device contact and the corresponding pin/contact surface, within the receptacle, and these couplings are electrically isolated from one another by the sealing rings.

FIG. 1 further illustrates lead 100 including an elongate body 130, which extends distally from connector 120 to a low voltage distal-most electrode de, two types of which are shown: one for what is known as a passive fixation lead (designated 'P'), and the other for what is known as an active fixation lead (designated 'A'). Although not shown, those skilled in the art understand that lead body 130 includes an elongate conductor extending therein, which couples distal-most electrode de, of either type of lead 100, to terminal connector pin 110, wherein, if lead 100 is the active fixation type A, rotation of pin 110 may be translated, via the conductor, to electrode de, which is shown formed as a helix for fixation in tissue at a target implant site. If lead 100 is the passive fixation type P, electrode de may be held at the target implant site via tines 135. Each type of lead 100 may further include one or more of electrodes e1, e2, e3, for example, mounted around lead body 130, wherein body 130 further includes a corresponding one or more elongate conductors (not shown), for example, to couple electrode e1 to contact surface cs1, to couple electrode e2 to contact surface cs2, and to couple electrode e3 to contact surface cs3. It should be noted that lead body 130 further includes insulative tubing that isolates the elongate conductors from one another. Various suitable configurations and constructions for each of electrodes de, e1-e3 are well known to those skilled in the art.

Either type of lead 100 may be configured according to any of the four exemplary configurations outlined in the chart of FIG. 1. In the first configuration, lead 100 includes just electrodes de and e1, wherein e1 is employed for pacing and sensing, in combination with electrode de, and for defibrillation, in which case electrode e1 is coupled to both first and second contact surfaces cs1, cs2 of connector 120. Alternately, electrode e1 may only function as a low voltage electrode being coupled to only first contact surface cs1. In the second configuration, lead 100 includes electrodes de, e1, and e3, wherein electrodes de and e1 function the same as in the first configuration, and electrode e3 is also employed for defibrillation, being coupled to contact surface cs3. In the third configuration, lead 100 includes electrodes de, e1, and e2, but electrode e1 is only employed for pacing and sensing, so is not coupled to contact surface cs2, instead electrode e2 is coupled to contact surface cs2. In the fourth configuration, lead 100 includes all of the illustrated electrodes de, e1-e3, wherein e1 is solely employed for pacing and sensing, and electrodes e2 and e3 are solely employed for defibrillation.

Although only the fourth configuration employs all of electrodes e1-e3, the aforementioned IS-4 industry standard requires the presence of all contact surfaces cs1-cs3 and all sealing surfaces ss1-ss4 for the other configurations, even though one or both of contact surfaces cs2 and cs3 may be inactive, to preserve the standard form of connector 120. Furthermore, it should be noted that the IS-4 industry standard also applies to low voltage only lead connectors, which have the same form as connector 120, but contact surfaces cs2 and cs3 are designated for low voltage electrodes, and/or other types of sensors. Thus, modular assemblies for lead connector 120 are desirable, to increase the flexibility in manufacturing a variety of implantable medical electrical lead configurations. Even though some constructions of lead connectors that incorporate modular assemblies, are known in the art, there is still a need for new constructions and manufacturing methods.

SUMMARY

Connector assemblies for implantable medical electrical leads, according to embodiments described herein, conform to one or more requirements, for example, of an industry standard. According to some embodiments, modular connector assemblies allow the construction thereof, for a given type of lead, active or passive, independent of a particular lead configuration, for example, to be compatible with any configuration from the group of configurations described above.

A connector assembly for an implantable medical electrical lead, according to some embodiments, includes a plurality of contact rings, and a bulk of insulation supporting the contact rings and isolating the contact rings from one another, wherein the bulk of insulation, preferably formed in two parts, for example, by injection molding, includes a plurality of sealing surfaces, and a shank that defines a distal end of the bulk of insulation. The assembly further includes one or more conductor pins extending within the bulk of insulation, wherein a distal end of each conductor pin protrudes distally from the bulk of insulation to be exposed alongside the shank thereof, and wherein an inner surface of each contact ring may have a proximal end of a corresponding conductor pin coupled thereto. A first sealing surface of the plurality extends from a proximal end of the bulk of insulation to a first, most proximal, ring of the plurality of contact rings, and the plurality of sealing surfaces, in conjunction with outer contact surfaces of the plurality of contact rings, which are interspersed therebetween, define a uniform outer diameter for the connector assembly, wherein the uniform outer diameter conforms to a requirement for the connector to mate with a connector receptacle of an implantable medical device. According to some preferred embodiments, the shank of the bulk of insulation has an asymmetric profile, for example, for a keyed fit within a lumen of a transition fitting that includes peripheral grooves to support the distal ends of the one or more conductor pins, which, if more than one in number, are preferably spaced apart from one another and spaced approximately equidistant from the central longitudinal axis of the assembly.

As alluded to above, and according to some preferred methods, the bulk of insulation is formed in two parts: a primary bulk of insulation overlaid by a secondary bulk of insulation. According to some embodiments, a subassembly includes the primary bulk of insulation, which includes a circuit-support segment and a shank segment extending distally from a distal end of the circuit-support segment. The circuit-support segment includes a plurality of open channels, each of which is configured to receive a corresponding one of the aforementioned conductor pins, each of which conductor pin forms a circuit with a corresponding one of the aforementioned contact rings; and wherein, when each contact ring is positioned around the circuit-support segment so that the corresponding conductor pin extends within the corresponding channel, a distal end of each pin is exposed alongside the shank segment of the primary bulk of insulation. The secondary bulk of insulation, which includes the aforementioned sealing surfaces, is injection molded around the primary bulk of insulation, after positioning each of the contact rings around the circuit-support segment of the primary bulk, and inserting each conductor pin within the corresponding open channel. The subassembly of the primary bulk of insulation further includes a core that extends within the bulk of insulation and is aligned along a central longitudinal axis thereof. The core augments a rigidity and structural integrity of the subassembly, and, according to some embodiments, forms a portion of another circuit of the subassembly, wherein the other circuit includes a terminal connector pin and another conductor pin. The terminal connector pin extends proximally from the core and circuit-support segment of the primary bulk of insulation, being coupled to a proximal end of the conductive core, for example, at a junction just proximal to a proximal end of the circuit-support segment, and the other conductor pin has a proximal end coupled to an outer surface of the core and extends therefrom, within the circuit-support segment of the primary bulk of insulation to a distal end thereof that is exposed alongside the shank segment of the primary bulk of insulation. This other conductor pin preferably includes a bend located between the proximal end thereof and a remainder of the pin, such that the remainder is spaced outward from the outer surface of the core.

Following formation of the secondary bulk of insulation around the subassembly that includes the terminal connector pin, the bulk of insulation extends around the junction between the connector pin and core, and the connector pin protrudes proximally from the proximal end of the bulk of insulation. According to alternate embodiments of connector assemblies and subassemblies that do not include the above-described terminal connector pin, a proximal portion of an elongate lead conductor is inserted through a lumen of the core, after the molding operation, and a terminal connector pin is then joined to the proximal portion of the lead conductor.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIGS. 2B-C are a perspective view and an end view, respectively, of a subassembly for the lead connector assembly, according to some embodiments of the present invention;

FIG. 5 is a cross-section view through a proximal end of a lead connector, according to some alternate embodiments;

FIG. 6 is a cross-section view through a proximal end of a lead connector, according to yet further embodiments;

FIG. 12A is a perspective view of a plurality of contact circuits for a connector assembly, according to some embodiments;

FIG. 12B is a perspective view of the contact circuits assembled together with the subassembly shown in FIG. 11A.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
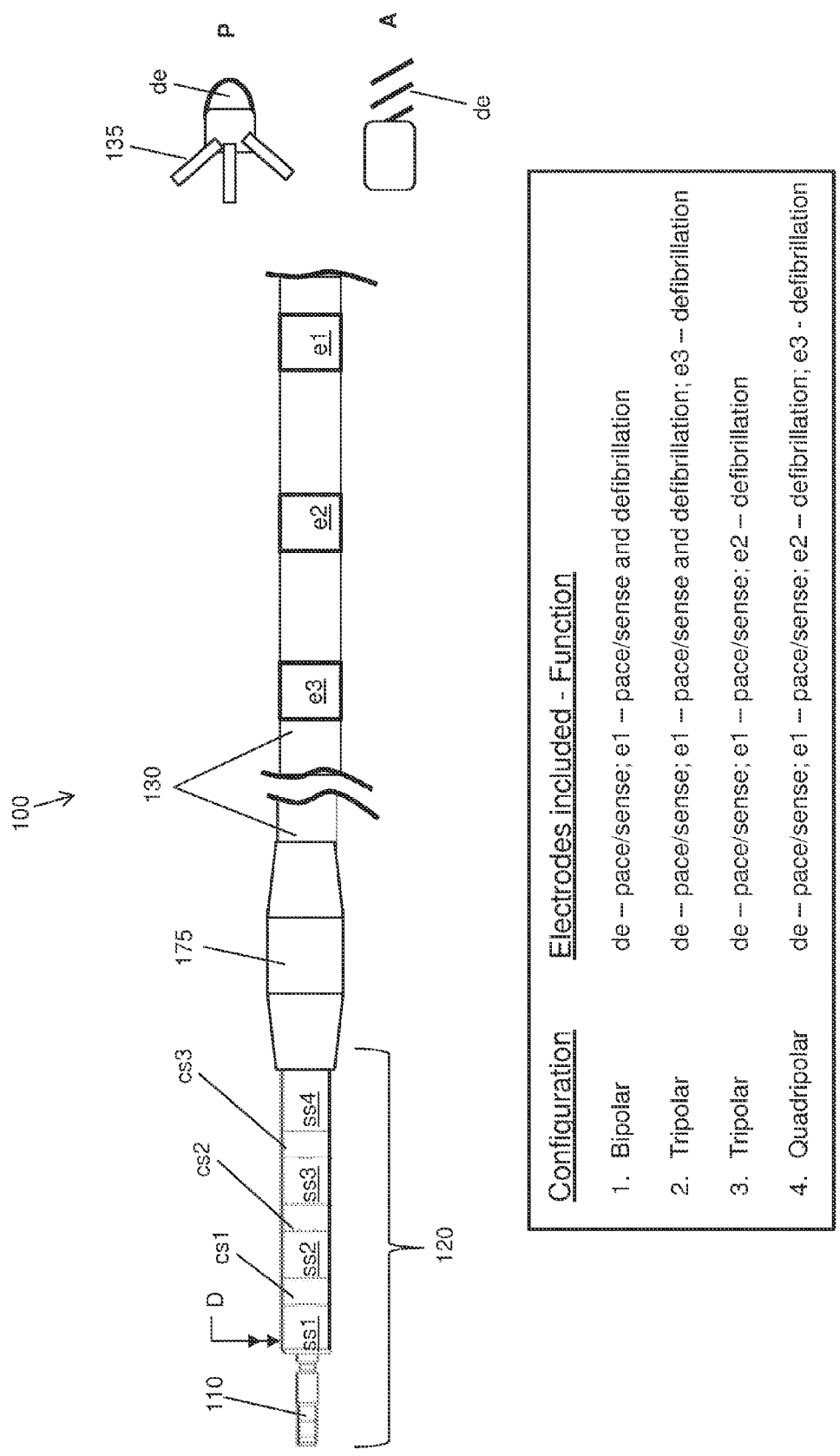
FIG. 1 is a schematic with a corresponding chart that describes various configurations of an exemplary implantable medical electrical lead.
Figure 2A:
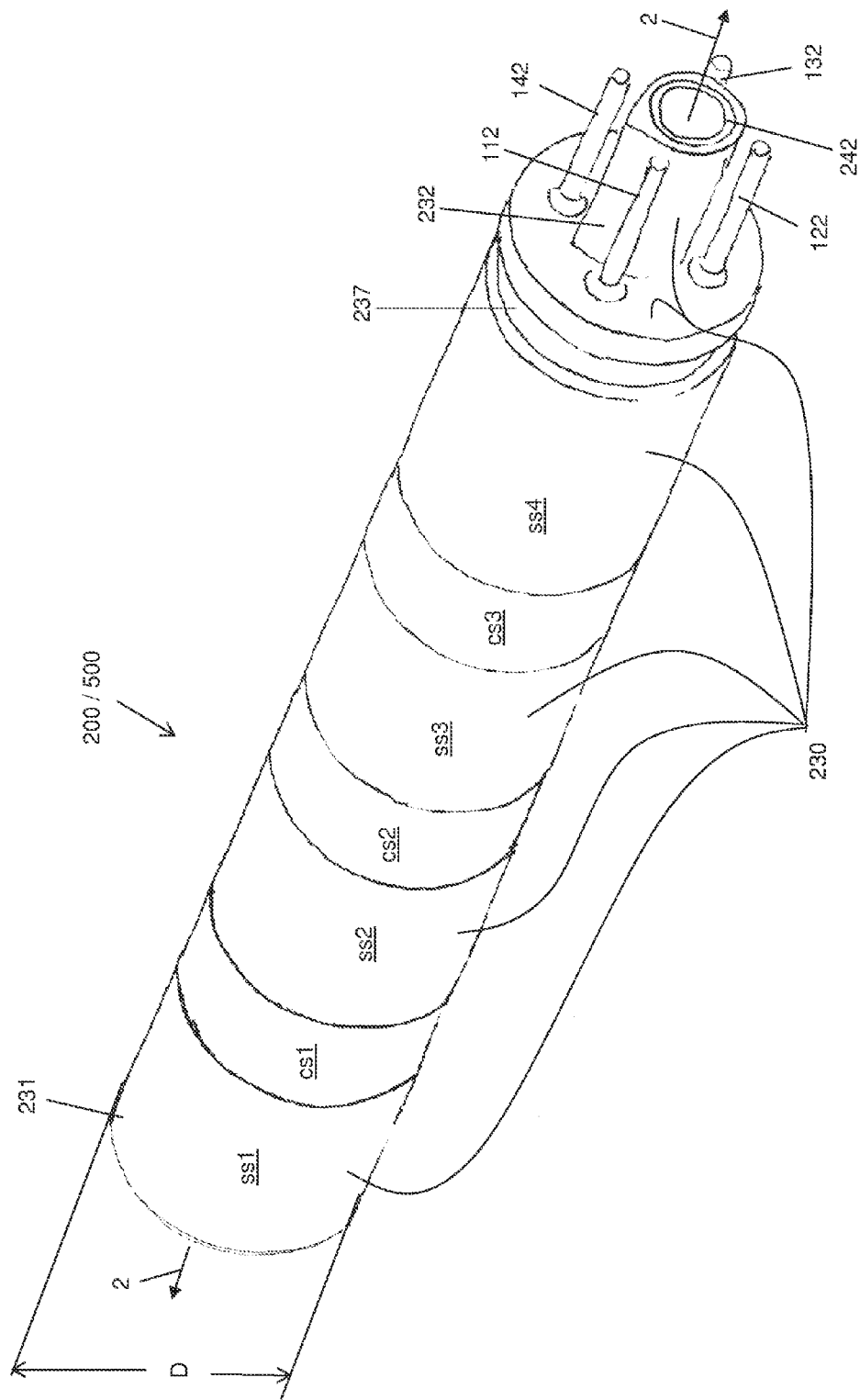
FIG. 2A is a perspective view of an implantable medical electrical lead connector assembly, according to some embodiments.

FIG. 2A is a perspective view of an implantable medical electrical lead connector assembly 200, according to some embodiments; and FIGS. 2B-C are a perspective view and an end view, respectively, of a subassembly for connector assembly 200, according to some embodiments, wherein first, second, and third contact rings 211, 212, 213 extend around a conductive core 240, and correspond to first, second, and third contact surfaces cs1, cs2, cs3, respectively. FIG. 2A illustrates assembly 200 including a central longitudinal axis 2, and having the aforementioned uniform outer diameter D that conforms to a requirement for a connector, in which assembly 200 is included (e.g., connector 120 of FIG. 1), to mate with a connector receptacle of an implantable medical device. FIG. 2A further illustrates assembly 200 including a bulk of insulation 230, which includes an outer surface divided into the above-described four sealing surfaces ss1, ss2, ss3, ss4. Insulation 230 extends around conductive core 240 and between contact surfaces cs1, cs2, cs3, and distal ends 112, 122, 132, 142 of conductor pins 11, 12, 13, 14 protrude distally therefrom. Bulk of insulation 230 may be formed from any suitable relatively hard, insulative, medical grade polymer material, an example of which is a 75D durometer thermoplastic polyurethane. FIG. 2B illustrates conductive core 240 extending from a proximal end 241 thereof to a distal end 242 thereof, along axis 2, wherein a proximal end 141 of conductor pin 14 is coupled to an outer surface of core 240, for example, by laser welding, to form a core circuit to which a terminal connector pin, for example, the above-described connector pin 110 (FIG. 1) may be coupled. A bend 21 is shown formed in pin 14, between the coupled proximal end 141 thereof and a remainder of pin 14, such that the remainder of pin 14, including distal end 142, is spaced outward from the outer surface of core 240. FIGS. 2B-C illustrate a proximal end 111, 121, 131 of each of the three other conductor pins 11, 12, 13 of the subassembly coupled to an inner surface of a corresponding ring 211, 212, 213, for example, by laser welding, to form three contact circuits. With reference to the end view of the subassembly in FIG. 2C, distal ends 112, 122, 132, 142 of conductor pins 11, 12, 13, 14 are spaced apart from one another and spaced approximately equidistant from central longitudinal axis 2, according to some preferred embodiments.

With further reference to FIG. 2B, each of conductor pins 11, 12, 13, like pin 14, has a bend 10 formed therein, between the coupled proximal end 111, 121, 131, and a remainder thereof, such that the remainder of each pin 11, 12, 13, including the corresponding distal end 112, 122, 132, is spaced inward from the inner surface of the corresponding contact ring 211, 212, 213, for example, to achieve the above-described spacing shown in FIG. 2C. However, according to some alternate embodiments, the inner surface of each contact ring 211, 212, 213 may be configured such that the coupling of the proximal end 111, 121, 131 of the corresponding pin 11, 12, 13 thereto spaces the remainder of the corresponding pin inward, and each bend 10 is not necessary. According to an exemplary embodiment, conductive core 240 is formed from medical grade stainless steel tubing, each ring 211, 212, 213 is formed from MP35N alloy, and each conductor pin 11, 12, 13, 14 is formed from a relatively rigid MP35N alloy wire. An optional jacket 20 of insulation is shown formed about pins 11, 12, 13 between the corresponding proximal and distal ends thereof.

Figure 3A:
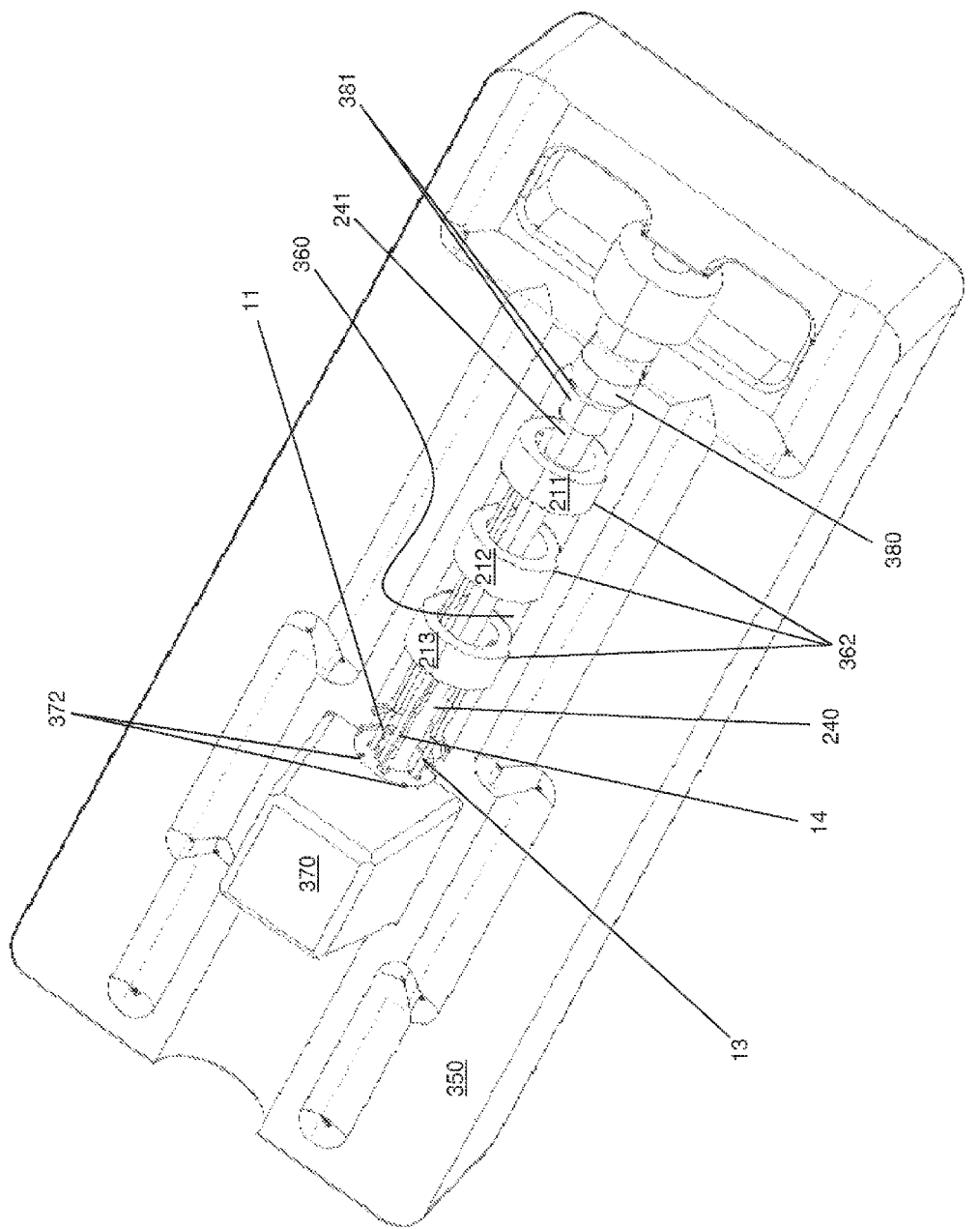
FIG. 3A is a perspective view of the subassembly assembled together with a mold assembly, according to some methods of the present invention.

With reference back to FIG. 2A, according to some embodiments, bulk of insulation 230 is formed by injection molding the insulative material around the subassembly shown in FIG. 2B. FIG. 3A is a perspective view of the above-described contact and core circuits of the subassembly assembled together with a mold assembly, according to some methods of the present invention. It should be noted that only one of two opposing and confronting mold blocks 350 is shown in FIG. 3A. FIG. 3A illustrates each contact ring 211, 212, 213 positioned in a corresponding recessed groove 362 of a cavity 360 formed in each mold block 350 of the mold assembly, with distal ends 112, 122, 132, 142 of conductor pins 11, 12, 13, 14 (FIG. 2B) inserted into corresponding bores of a core plug 370 of the mold assembly. (The opposing mold block, which is not shown, includes the other, opposing, portion of cavity 360.) Conductive core 240 is shown positioned within a perimeter of each ring 211, 212, 213 in cavity 360, with distal end 242 (FIG. 2B) of core 240 inserted within another bore of core plug 370. With further reference to FIG. 2A, it may be appreciated that this other bore of core plug 370 has an asymmetric profile so that a distal end 232 of insulation 230, which is formed around distal end 242 of core 240 has the asymmetric profile (e.g., a tear drop shape) that is shown in FIG. 2A, according to some embodiments.

Figure 3B:
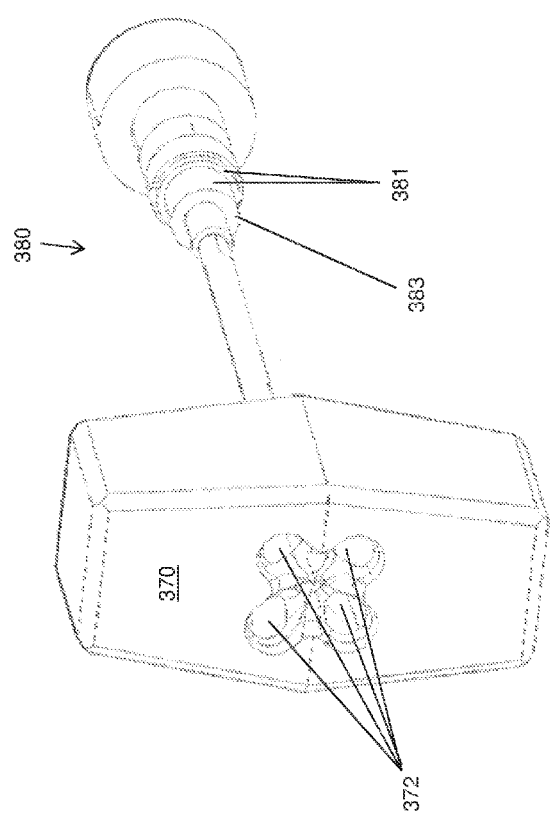
FIG. 3B is a perspective view of portions of the mold assembly, according to some embodiments.

FIG. 3A further illustrates core plug 370 including injection gates 372 formed therein to receive the flow of the insulative material therethrough; and, in FIG. 3B, openings of gates 372 may be seen on an opposite side of core plug 370. When the insulative material is injected through gates 372 and into cavity 360, around the core and contact circuits assembled therein, each recessed groove 362 prevents the corresponding contact ring 211, 212, 213 from being moved by the force of the flow of the injection, and a core pin 380 of the mold assembly, which extends within conductive core 240, prevents the movement of conductive core 240, and provides a shut-off at either end 241, 242 of core 240. FIG. 3B is a perspective view of core pin 380 and core plug 370 separated from the rest of the mold assembly. FIG. 3B illustrates core pin 380 including a shoulder 383, against which proximal end 241 of conductive core 240 abuts, as shown in FIG. 3A, and an enlarged stepped portion 381, which extends proximally from shoulder 383.

Figure 3C:
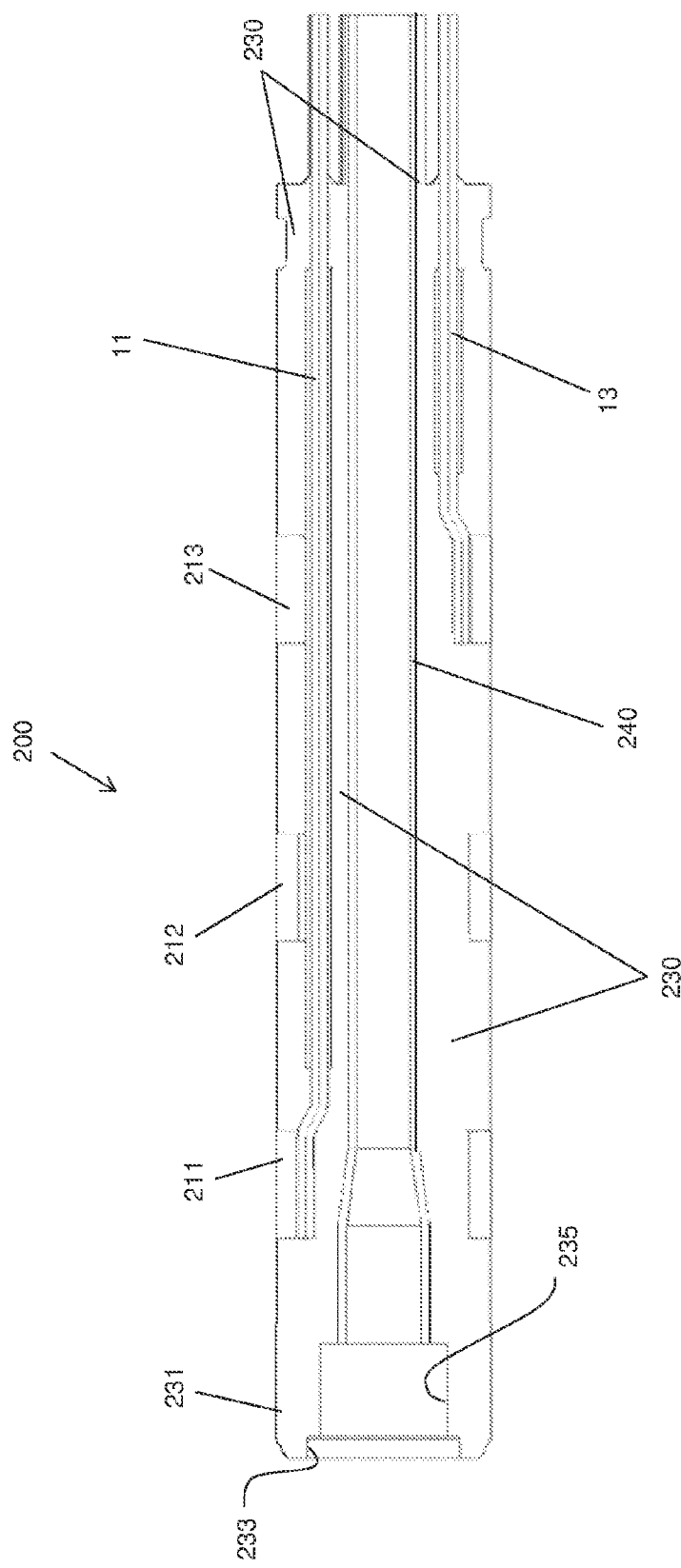
FIG. 3C is a cross-section view through the assembly of FIG. 2A, according to some embodiments.

With reference to FIG. 3C, which is a cross-section view through assembly 200, it may be appreciated that the molded bulk of insulation 230 holds together the core and contact circuits and isolates the core and contact circuits from one another. Furthermore, enlarged stepped portion 381 of core pin 380 creates a bore 235 and counter bore 233 opening in insulation bulk 230, at a proximal end 231 thereof, which accommodates a retainer component 410 that holds terminal connector pin 110 in place, relative to assembly 200, according to some embodiments, for example, like that illustrated in FIG. 4A.

To facilitate holding rings 211, 212, 213 in recessed grooves 362 of mold cavity 360, according to the above-described method, each contact ring 211, 212, 213 has an enlarged outer diameter, relative to the injection molded material; so, a manufacturing step to reduce the outer diameter of rings 211, 212, 213, and, in some cases, to also remove molding byproducts at the outer diameter of the injection molded material (e.g., parting line removal), follows the injection molding. According to some methods, a grinding method, for example, a centerless grinding process known to those skilled in the art, is employed to bring the outer diameter of the molded assembly, along an entire length of contact surfaces cs1-cs3 and sealing surfaces ss1-ss4, down to the uniform outer diameter D shown in FIG. 2A.

With further reference to FIG. 2A, assembly 200, being modular, may be incorporated by any one of a number of lead types and configurations, for example, like the types and configurations described above in conjunction with FIG. 1. With reference to FIG. 1, if assembly 200 is employed by lead 100 of the passive fixation type P, terminal connector pin 110 may be an element of the core circuit—coupled to conductive core 240, which is coupled to conductor pin 14, for example, in the manner described below in conjunction with FIGS. 4A-B, wherein each elongate conductor of the lead is coupled to a corresponding conductor pin distal end 112, 122, 132, 142, to electrically couple each electrode de, e1, e2, e3 to connector 120. Or, a modified assembly 200 may be employed in the manner described in conjunction with FIG. 5. If assembly 200 is employed by lead 100 of the active fixation type A, the coupling of each contact surface cs1, cs2, cs3 to a corresponding electrode e1, e2, e3 is accomplished via the coupling of the corresponding conductor pin distal end 112, 122, 132 to the corresponding lead conductor, but the lead conductor that is coupled to distal-most electrode de (e.g., a helix electrode) is directly coupled to terminal connector pin 110, for example, as described below in conjunction with FIG. 6. For either type of lead, a transition fitting, several embodiments of which will be described below in conjunction with FIGS. 7A-9, may be joined to bulk of insulation 230 to support conductor pin distal ends 112, 122, 132, 142 and associated couplings thereof to the lead conductors. With further reference to FIG. 2A, in conjunction with FIG. 1, an external groove 237 is formed in insulation bulk 230, just distal to fourth sealing surface ss4, to accommodate coupling of a connector sleeve 175, for example, formed from medical grade silicone rubber, that extends from lead body 130 to connector 120.

Figure 4A:
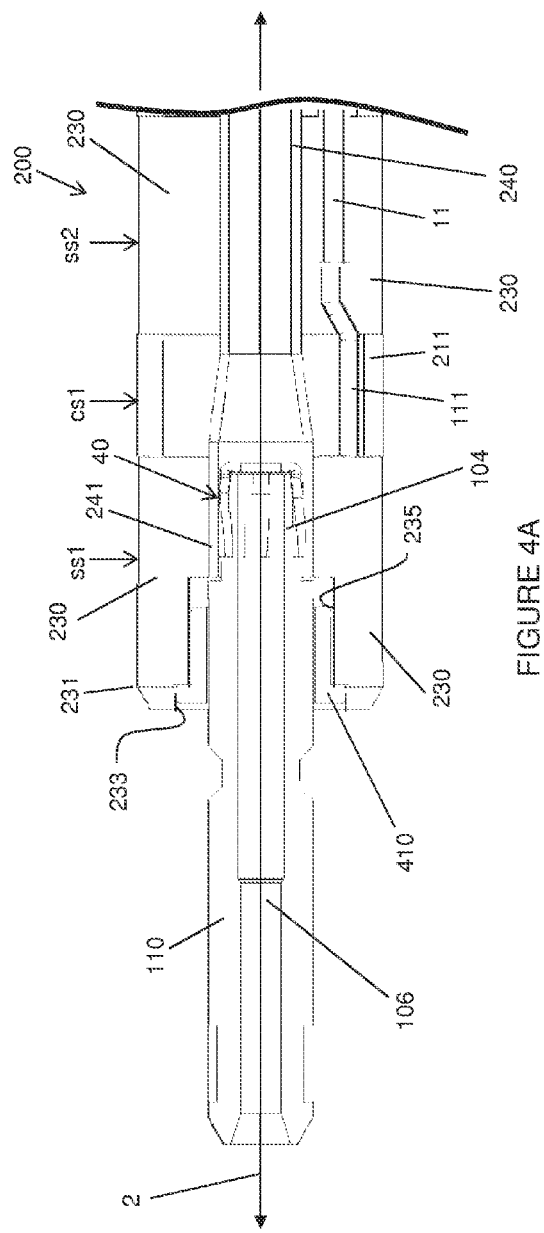
FIG. 4A is a cross-section view through a proximal end of a lead connector, according to some embodiments.
Figure 4B:
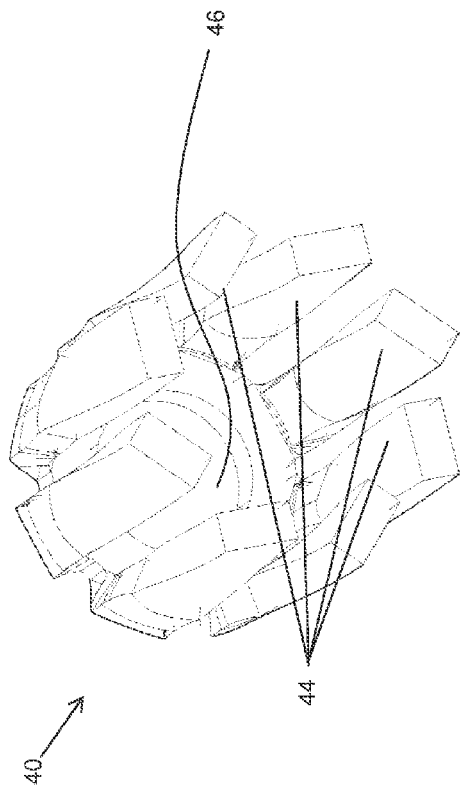
FIG. 4B is a perspective view of a multi-point contact employed in the assembly of the lead connector of FIG. 4A, according to some embodiments.

FIG. 4A is a cross-section view through a proximal end of a lead connector that includes assembly 200, according to some embodiments. FIG. 4A illustrates the core circuit of assembly 200 including terminal connector pin 110, which is coupled to conductive core 240. According to the illustrated embodiment, proximal end 241 of conductive core 240 defines a lumen in which a multi-point contact 40 is mounted, and multi-point contact 40 engages a shank 104 of connector pin 110, within the lumen of proximal end 241, to couple connector pin 110 to conductive core 240. FIG. 4B is a perspective view of multi-point contact 40, according to some embodiments. FIG. 4B illustrates multi-point contact 40 including a plurality of spring-loaded fingers 44 spaced apart around an aperture 46 of contact 40. With reference to FIG. 4A, aperture 46 is approximately aligned along central axis 2, when multi-point contact 40 is press fit within the lumen of conductive core 240, so that fingers 44 create multiple contact points between shank 104 and conductive core 240. According to an exemplary embodiment, multi-point contact 40 is formed from a sheet of MP35N alloy having a thickness of approximately 0.005 inch, for example, by a stamping process. FIG. 4A further illustrates terminal connector pin 110 including a through lumen 106 that is in fluid communication with the lumen of conductive core 240, via aperture 46 of multi-point contact 40, for example, to allow passage of an instrument, such as a stylet, therethrough and into a lumen of lead body 130 (FIG. 1).

FIG. 5 is a cross-section view through a proximal end of a lead connector, according to some alternate embodiments, which includes a modular assembly 500. With reference back to FIG. 2A, assembly 500 has the same external configuration as assembly 200, and may be manufactured in approximately the same manner, as described in conjunction with FIGS. 3A-B, but the core circuit of assembly 500 includes a different configuration of conductive core 240. With reference to FIG. 5, a proximal end 541 of a conductive core 540 in assembly 500 is not flared like proximal end 241 of conductive core 240, and conductive core 540 has a shorter length, along axis 2, than core 240. FIG. 5 illustrates the core circuit of assembly 500 including terminal connector pin 110 coupled to conductive core 540 by a coil-type multi-point contact 50, wherein contact 50 includes a distal portion 52, which is fitted within a lumen defined by proximal end 541 of conductive core 540, and a proximal portion 51 that extends proximally from proximal end 541 of conductive core 540 to engage shank 104 of connector pin 110. According to the illustrated embodiment, proximal portion 51 of contact 50 is mounted around shank 104, for example, having been spun thereon and welded thereto, and distal portion 52 of contact 50 is compressed within the lumen of conductive core 541 to create multiple contact points therewith. According to an exemplary embodiment, contact 50 is formed from an tight-wound MP35N wire that has a wire diameter of approximately 0.005 inch. FIG. 5 further illustrates a lumen 56 of contact 50 bridging lumen 106 of connector pin 110 and the lumen of conductive core 540, for example, to allow passage of an instrument therethrough as described above.

As mentioned above, the core circuit configurations associated with FIGS. 4A-5 may be employed by lead 100 of the passive fixation type P (FIG. 1), wherein, with reference back to FIG. 2A, distal-most electrode de is coupled to terminal connector pin 110, via an elongate conductor of the lead coupled to contact pin distal end 142 of the core circuit. FIG. 6 is a cross-section view through a proximal end of a lead connector, which includes assembly 200, according to embodiments that are suitable for employment by lead 100 of the active fixation type A. FIG. 6 illustrates an elongate coiled lead conductor 600 coupled to terminal connector pin 110, for example, being mounted around shank 104 and laser welded thereto, wherein conductor 600 extends distally from the lead connector and through lead body 130 to couple with distal-most electrode de, for example, of the helix type illustrated in FIG. 1 for active fixation type lead A. Thus, according to the embodiment of FIG. 6, conductor 600 couples distal-most electrode de to connector pin 110, without the core circuit interface employed by passive fixation type lead P, so as to form a drive shaft with connector pin 110, which may be rotated to extend and retract helix electrode de relative to lead body 130, according to constructions and methods known in the art.

Figure 7A:
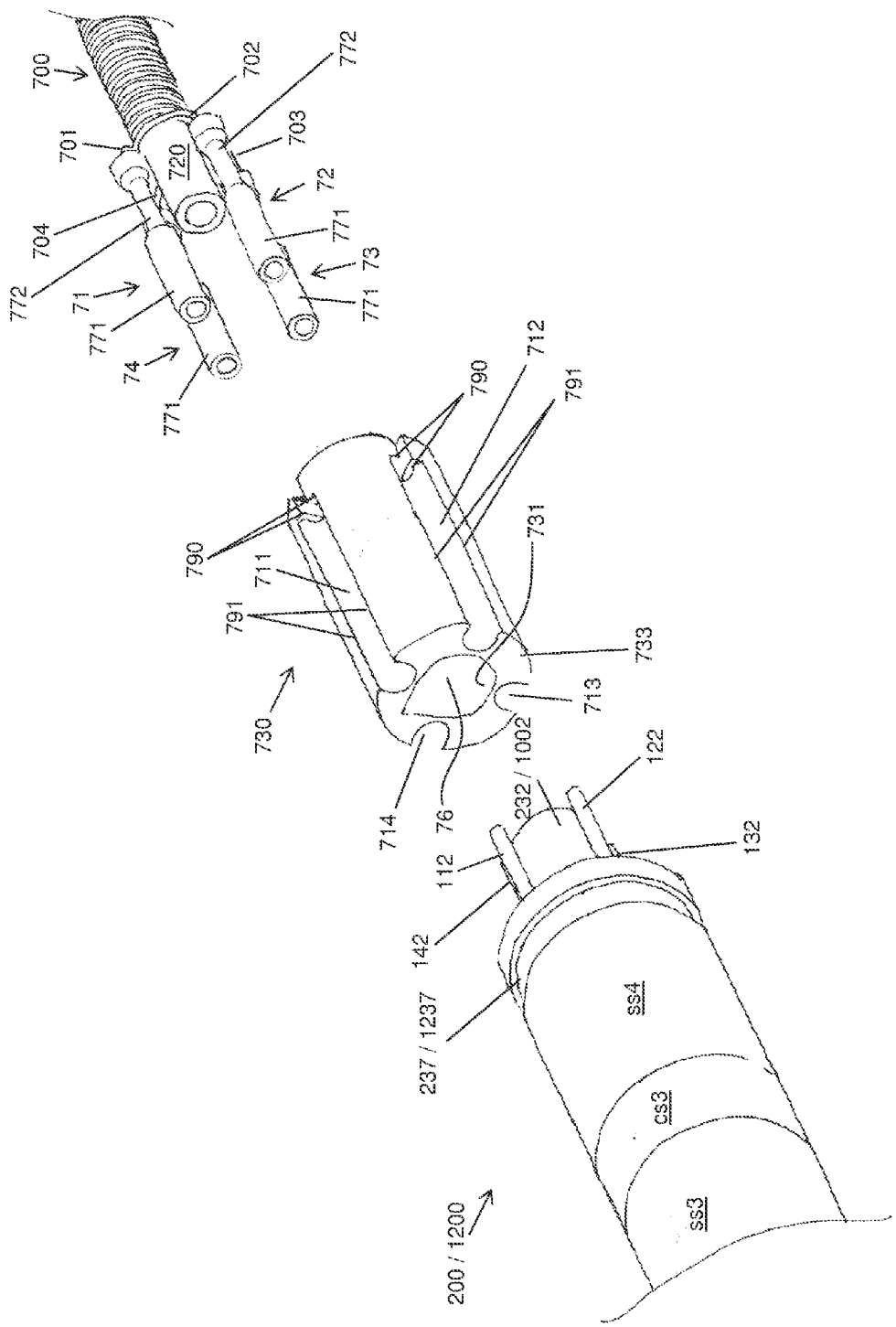
FIG. 7A is an exploded perspective view of a lead connector assembly, according to some embodiments.
Figure 7B:
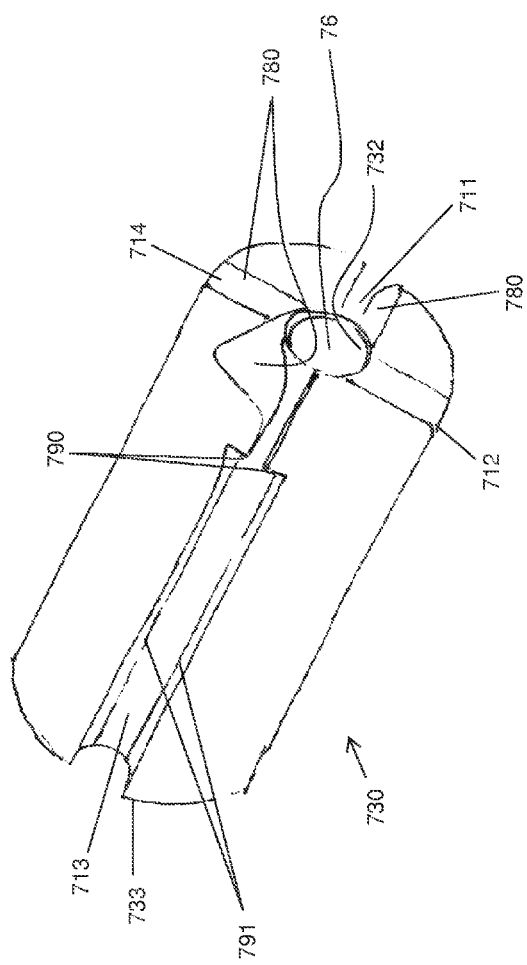
FIG. 7B is a perspective view of a transition fitting of the lead connector assembly, according to some embodiments.
Figure 7C:
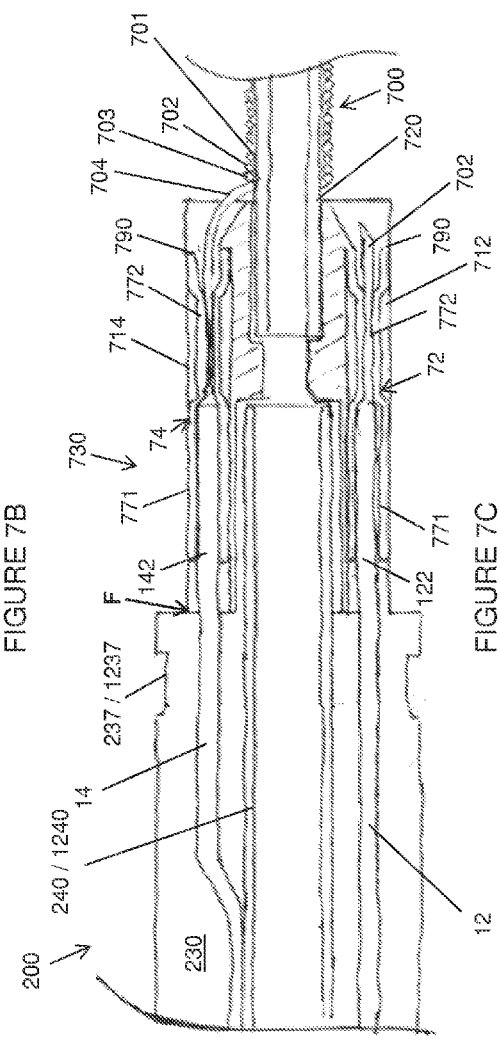
FIG. 7C is a cross-section view through the transition fitting portion of the assembly of FIG. 7A, according to some embodiments.

FIG. 7A is an exploded perspective view of a connector assembly that includes assembly 200 and a transition fitting 730, according to some embodiments; and FIG. 7B is a perspective view of transition fitting 730, according to some embodiments. FIG. 7A illustrates transition fitting 730 including a lumen 76 and four peripheral grooves 711, 712, 713, 714, each of which is positioned and sized to support conductor pin distal ends 111, 112, 113, 114 when transition fitting 730 is joined to assembly 200, as illustrated in the cross-section view of FIG. 7C. Transition fitting 730 is preferably formed from the same insulative material that forms bulk of insulation 230 of assembly 200, and a proximal end 733 thereof may be fused to bulk of insulation 230 by a solvent or thermal process known in the art, for example, at an abutting interface F (FIG. 7C). A proximal portion 731 of lumen 76, seen in FIG. 7A, has an asymmetric profile to fit around the similar asymmetric profile of distal end 232 of insulation 230. These asymmetric profiles provide a keyed fit, for example, to guide proper alignment of grooves 711-714 with conductor pin distal ends 111, 112, 113, 114 when joining fitting 230 to assembly 200. FIGS. 7A and 7C also show a proximal portion of a lead body, for example, lead body 130 of lead 100 (FIG. 1), passive fixation type P, wherein a multi-conductor coil 700 thereof extends around an inner insulation tubing 720 thereof, and is configured for coupling to conductor pin distal ends 112, 122, 132, 142 of assembly 200. FIG. 7B shows a distal portion 732 of lumen 76, which is sized to receive inner insulation tubing 720, for example, as shown in FIG. 7C. Although not shown, it should be understood that lead body 130 also includes an outer insulation tubing that extends over coil 700 to isolate coil 700 from an environment external to lead 100.

FIG. 7A further illustrates multi-conductor coil 700 including at least four individual conductor coil filars 701, 702, 703, 704, for coupling electrodes e1, e2, e3, de, respectively, to the corresponding conductor pin distal end 112, 122, 132, 142, for example, to accommodate the fourth lead configuration (quadripolar) in the chart of FIG. 1. However, with further reference to the chart of FIG. 1, assembly 200 and transition fitting 730, being modular, can also be employed for any of the other three lead configurations. For example, in the second, tripolar configuration, lead conductor coil filar 704 couples distal-most electrode de to terminal connector pin 110 via a coupling with conductor pin 14, lead conductor coil filars 701 and 702 couple first electrode e1 to both first and second contact surfaces cs1, cs2, via couplings with conductor pins 11 and 12, and lead conductor coil filar 703 couples third electrode e3 to third contact surface cs3, via conductor pin 13. In the first, bipolar configuration, conductor pins 11, 12 and 14 of assembly 200 are employed in the same manner, but conductor pin 13 remains uncoupled so that third contact surface cs3 is inactive.

With further reference to FIGS. 7A and 7C, each conductor pin distal end 112, 122, 132, 142 may be coupled to the corresponding conductor coil filar 701, 702, 703, 704, within the corresponding groove 711, 712, 713, 714 of transition fitting 730, by means of a corresponding one of junction sleeves 71, 72, 73, 74. According to the illustrated embodiment, each junction sleeve 71-74 includes a crimp portion 772, each of which is shown crimped to the corresponding conductor coil filar 701-704, and a weld portion 771, each of which is configured to receive the corresponding conductor pin distal end 112, 122, 132, 142 therein, for laser welding thereto. According to an exemplary embodiment, each junction sleeve 71-74 is formed from MP35N alloy, and has an inner diameter of approximately 0.012 inch and an outer diameter of approximately 0.02 inch. With reference to FIG. 7B, in some embodiments, a distal entry into each groove 711-714 has a rounded edge 780 to provide strain relief for the corresponding conductor coil filar 701-704, just distal to the crimp thereof within the corresponding sleeve 71-74. According to some preferred embodiments, each groove 711-714 is further configured with tabbed opposing edges 791 and shoulders 790 that can help to retain each junction sleeve 71-74 in the corresponding groove 711-714. According to some methods, after crimping each sleeve 71-74 to the corresponding filar 701-704, each sleeve 71-74 may either be pushed radially, past the tabs of edges 791, and into the corresponding groove 711-714 for a snap fit therein, or slid into the corresponding groove 711-714 from proximal end 733 of transition fitting 730, for example, until each sleeve abuts shoulders 790 of the corresponding groove 711-714.

Following the coupling of each lead conductor to the corresponding contact pin of the connector assembly, the aforementioned connector sleeve 175 (FIG. 1) is assembled around the above-described couplings, for example, supported by transition fitting 730, and is secured to assembly 200 by interlocking a proximal end thereof in external groove 237 of bulk of insulation 230, then connector sleeve 175 is bonded to an outer insulation layer of lead body 130, for example, with a silicone medical adhesive. Connector sleeve 175 isolates the couplings from the environment external to lead 100, and may provide a degree of strain relief between lead body 130 and fitting 730. However, a transition fitting that provides additional strain relief may be substituted for fitting 730, according to some alternate embodiments, for example, as shown in FIGS. 8 and 9.

Figure 8:
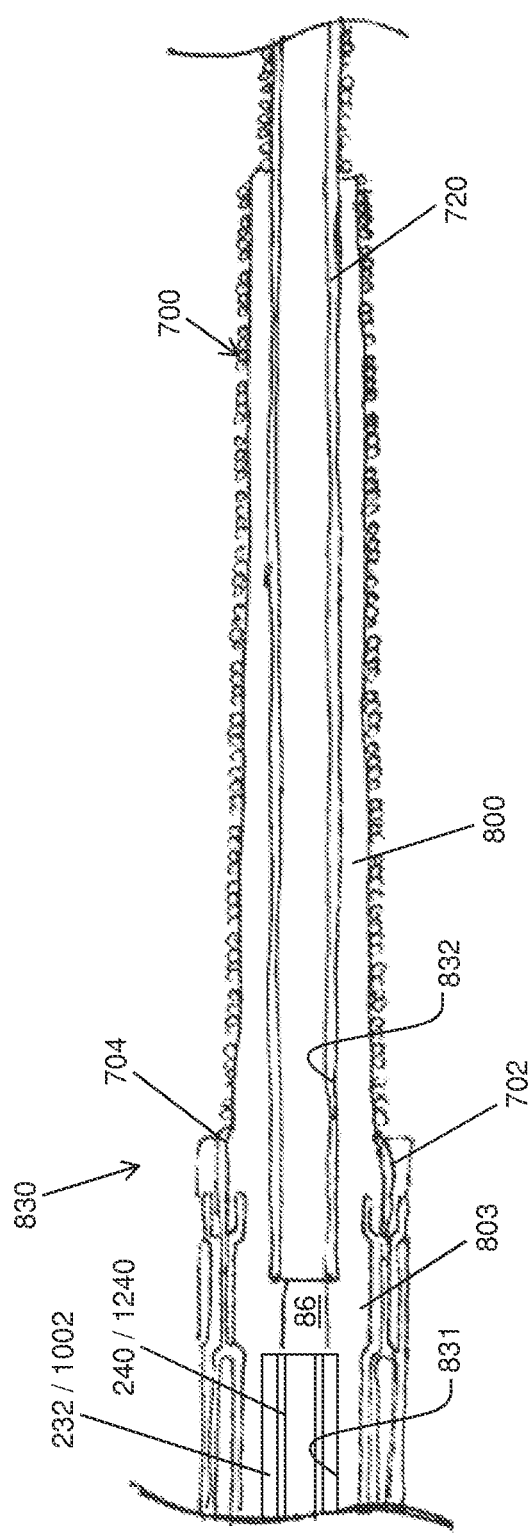
FIG. 8 is a cross-section view through a transition fitting portion of a lead connector assembly, according to some alternate embodiments.
Figure 9:
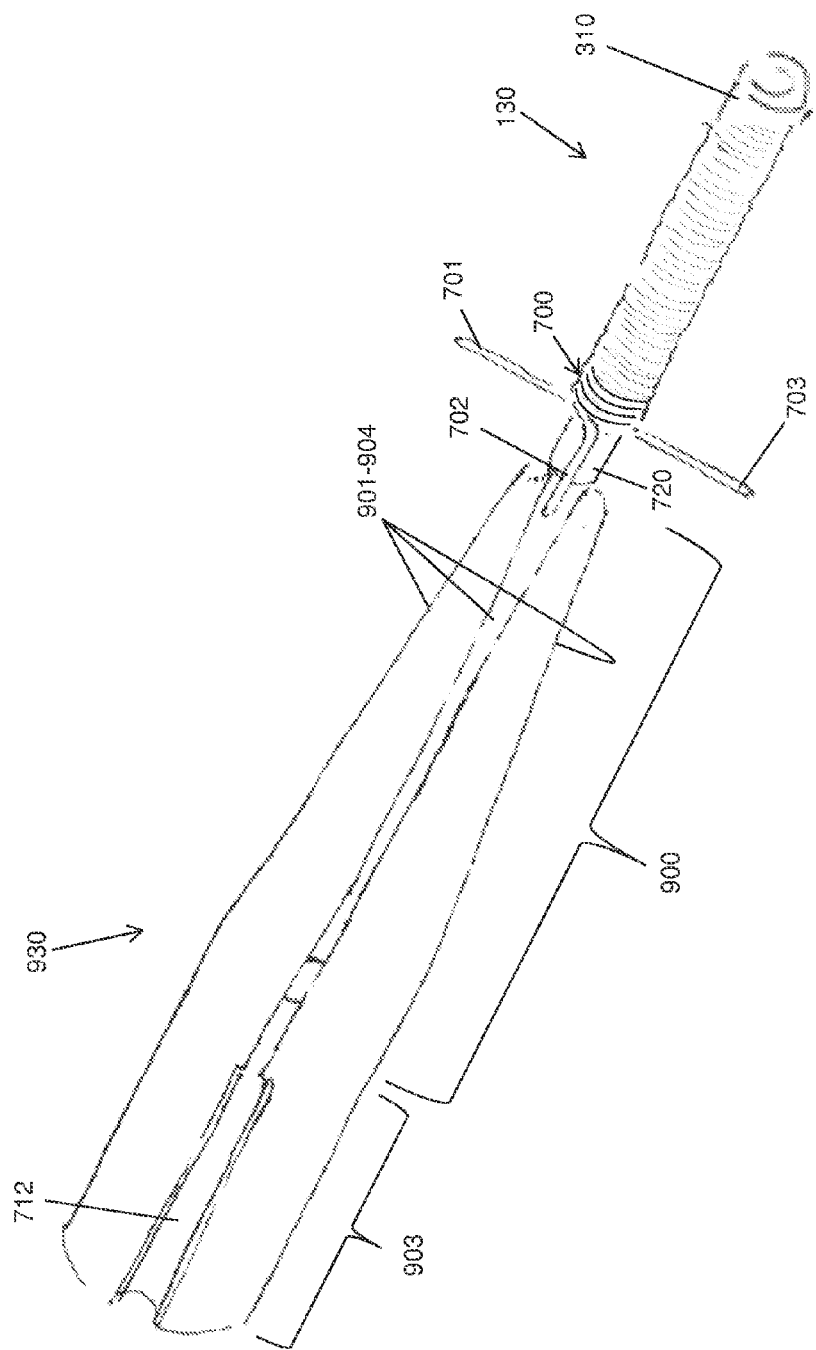
FIG. 9 is a perspective view of another transition fitting, according to yet further embodiments, positioned adjacent a lead body for assembly therewith.

FIG. 8 is a cross-section view through a transition fitting 830 of a lead connector assembly, according to some alternate embodiments; and FIG. 9 is a perspective view of another transition fitting 930, according to yet further embodiments, positioned adjacent to lead body 130 for assembly therewith. FIG. 8 illustrates transition fitting 830 including a grooved portion 803, which is similar to transition fitting 730, and a strain relief portion 800, which extends distally from grooved portion 803, and which has a tapered profile about which multi-conductor coil 700 is fitted. FIG. 8 further illustrates a lumen 86 of transition fitting 830 including a proximal portion 831, similar to proximal portion 731 of lumen 76 of fitting 730, and a distal portion 832; distal ends 232, 242 of insulative bulk 230 and conductive core 240, respectively, of assembly 200 (FIG. 2A) are fitted with proximal portion 831 of lumen 86, and inner insulation tubing 720 is fitted within distal portion 832 of lumen 86 such that strain relief portion 800 of fitting 830 is sandwiched between inner insulation tubing 720 and coil 700. FIG. 9 illustrates transition fitting 930 including a grooved portion 903, which is similar to transition fitting 730, and a strain relief portion 900, which extends distally from grooved portion 903, and which has slots 901-904 formed therein. According to the illustrated embodiment, strain relief portion 900 is sized to fit around inner insulation tubing 720, multi-conductor coil 700, and an outer insulation tubing 310 of lead body 130, which overlays coil 700; and each slot 901-904 allows a corresponding conductor coil filar 701-704 to be received in a corresponding groove 711-714 of grooved portion 903, as lead body 130 is assembled together with fitting 930, as can be seen for conductor 702 in FIG. 9. Although not shown, it should be understood that a lumen of transition fitting 930 includes a proximal portion similar to that of transition fitting 730 to join with assembly 200.

Figure 10:
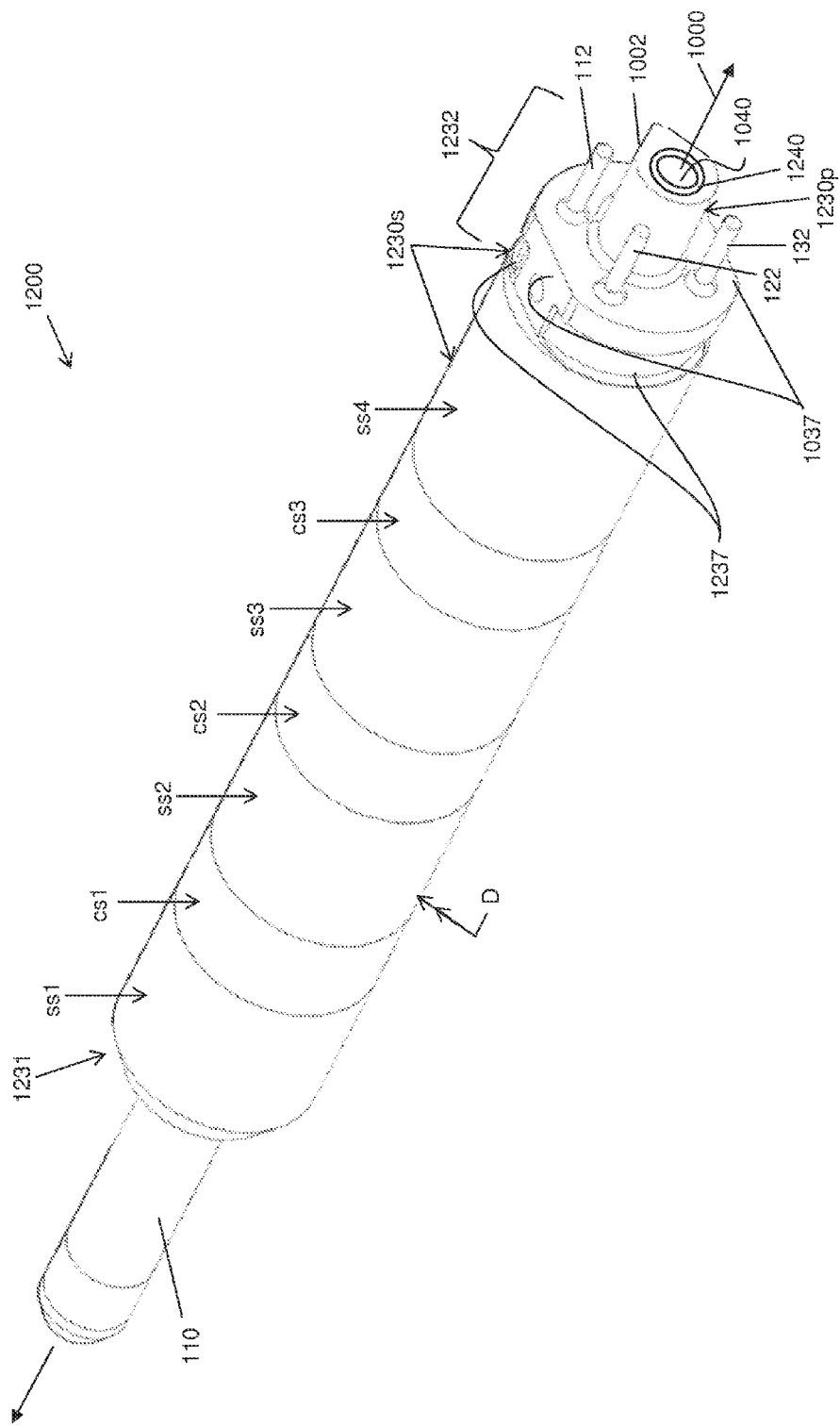
FIG. 10 is a perspective view of a connector assembly for an implantable medical electrical lead, according to some alternate embodiments.

FIG. 10 is a perspective view of a lead connector assembly 1200, according to some alternate embodiments, for example, suitable for the passive fixation type P of implantable medical electrical lead 100 described above in conjunction with FIG. 1. Assembly 1200 includes a plurality of contact circuits and a bulk of insulation, which is preferably formed in two parts: a primary bulk of insulation 1230p overlaid by a secondary bulk of insulation 1230s, for example, having been overmolded onto primary bulk 1230p and around the contact circuits. Each contact circuit, similar to those included in the above described assemblies 200, 500, includes a conductor pin 11, 12, 13 electrically coupled to a corresponding contact surface cs1, cs2, cs3, wherein distal ends 112, 122, 132 of pins 11, 12, 13 protrude distally from the bulk of insulation. Also like the above-described assemblies 200, 500, assembly 1200 has sealing surfaces ss1, ss2, ss3, ss4, each of which extends alongside a corresponding contact surface cs1, cs2, cs3. Each sealing surface ss1-ss4 and each contact surface cs1-cs3 defines uniform outer diameter D, which is required for assembly 1200 to conform to the aforementioned requirement. However, according to a preferred method described below, a grinding process is not required to achieve the uniform outer diameter D for assembly 1200.

FIG. 10 illustrates the bulk of insulation including a shank 1232 that defines a distal end thereof, wherein shank 1232 includes a proximal portion defined by a groove 1237 and opposing flats 1037, and a distal portion defined by an asymmetric profile 1002, alongside which distal ends 112, 122, 132 of conductor pins 11, 12, 13 extend. Asymmetric profile 1002 is similar to that described above for insulation distal end 232 of connector assembly 200, for example, being tear drop shaped, to mate with proximal portion 731 of lumen 76 of transition fitting 730 so that each distal end 112, 122, 132 is located in a corresponding peripheral groove 711-713, wherein each groove 711-713 may support a coupling between a corresponding pin distal end 112, 122, 132 and a corresponding conductor of a lead (depending upon the configuration of the lead, for example, selected from the configurations described above in conjunction with FIG. 1) in the manner described above in conjunction with FIGS. 7A-C. Likewise, connector sleeve 175 (FIG. 1), which isolates the couplings in grooves 711-713, and which provides some strain relief, as described above, may be configured to interlock within groove 1237 of assembly 1200. Furthermore, it should be appreciated that connector assembly 1200 is compatible for assembly together with either of the above-described alternative transition fittings 830, 930 (FIGS. 8-9), in lieu of fitting 730.

Figure 11A:
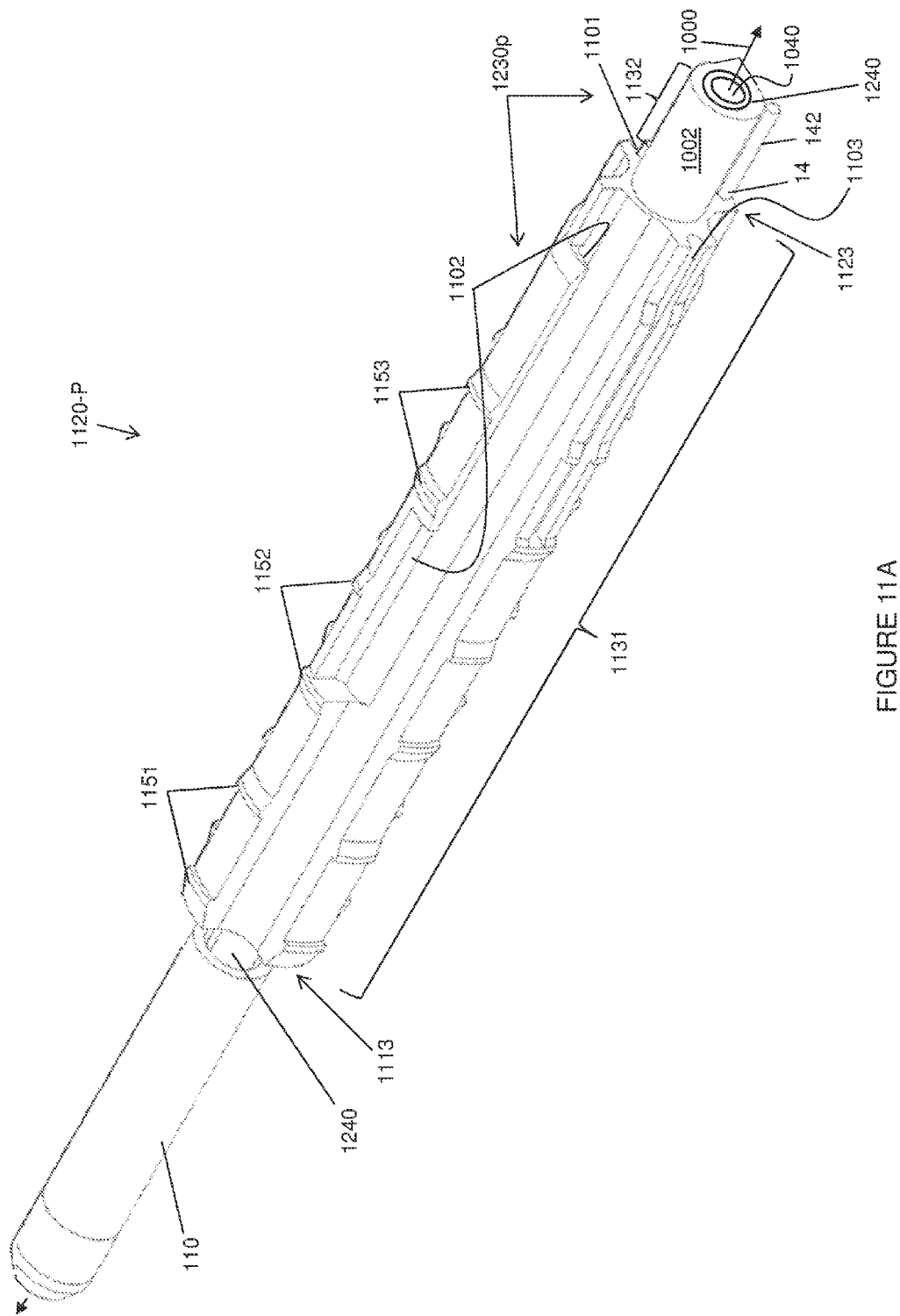
FIG. 11A is a perspective view of a subassembly for a connector assembly, for example, like that shown in FIG. 10, according to some embodiments.
Figure 11B:
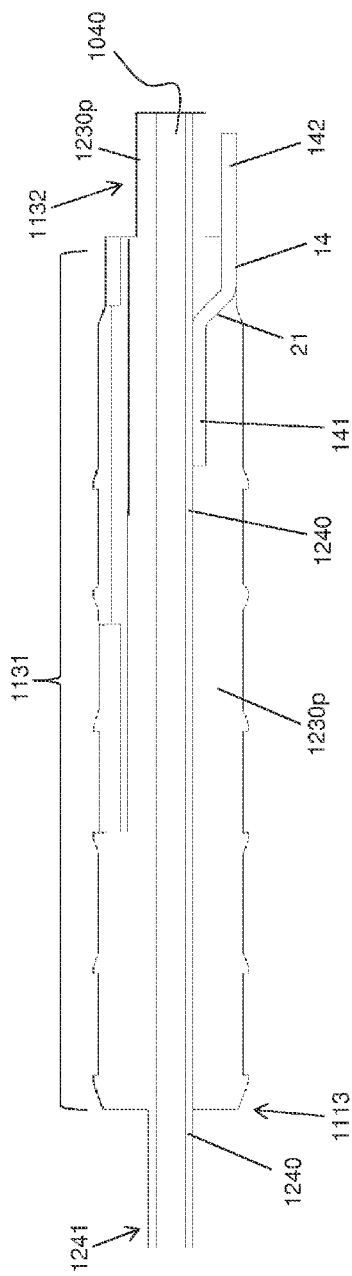
FIG. 11B is a cross-section view through the subassembly of FIG. 11A, according to some embodiments.

FIG. 11A is a perspective view of a subassembly 1120-P, for connector assembly 1200, that includes primary bulk of insulation 1230p. FIG. 11A illustrates primary bulk 1230p including a circuit support segment 1131 and a shank segment 1132, which extends distally therefrom along a central longitudinal axis 1000 shared by assembly 1200 and subassembly 1120-P, wherein shank segment 1132 forms asymmetric distal portion 1002 of shank 1232 (FIG. 10). FIG. 11A further illustrates subassembly 1120-P including a core 1240 that extends within the primary bulk of insulation 1230p, being aligned along central longitudinal axis 1000. Core 1240 augments a rigidity and structural integrity of subassembly 1120-P and forms a portion of a core circuit that includes terminal connector pin 110 and conductor pin 14. According to an exemplary embodiment, core 1240 is formed from medical grade stainless steel, and a proximal end 141 of conductor pin 14 may be coupled to an outer surface of core 1240, for example, in a similar manner to that described above for core 240 in conjunction with FIG. 2B. Conductor pin 14 preferably includes bend 21 formed therein, between the coupled proximal end 141 thereof and a remainder of pin 14, such that the remainder of pin 14, including distal end 142, is spaced outward from the outer surface of core 1240 as can be seen in the cross-section view of FIG. 11B. FIGS. 11A-B show distal end 142 of conductor pin 14 extending alongside shank segment 1132 so that distal end 142 will be exposed, in assembly 1200, for coupling terminal connector pin 110 to a corresponding conductor of a passive fixation type P lead. With reference back to FIG. 10, distal ends 112, 122, 132, 142 of conductor pins 11, 12, 13, 14 are spaced apart from one another and spaced approximately equidistant from central longitudinal axis 1000, so that each distal end 112, 122, 132, 142 may be located in a corresponding peripheral groove 711-714 of transition fitting 730, for coupling with a corresponding lead conductor, as described above.

With further reference to FIGS. 11A-B, terminal connector pin 110 is coupled to a proximal end 1241 of conductive core 1240, for example, by a laser weld junction located in proximity to a proximal end 1113 of circuit support segment 1131 of primary bulk of insulation 1230p. Primary bulk of insulation 1230p may be injection molded around core 1240 and conductor pin 14, either before or after forming the junction between connector pin 110 and core 1240, preferably after. FIGS. 10 and 11A-B further illustrate core 1240 including an optional lumen 1040 that extends longitudinally along axis 1000 and may be in fluid communication with lumen 106 of terminal connector pin (FIGS. 4A, 5, 6), for example, to allow passage of an instrument, such as a stylet or guidewire, therethrough.

Figure 11C:
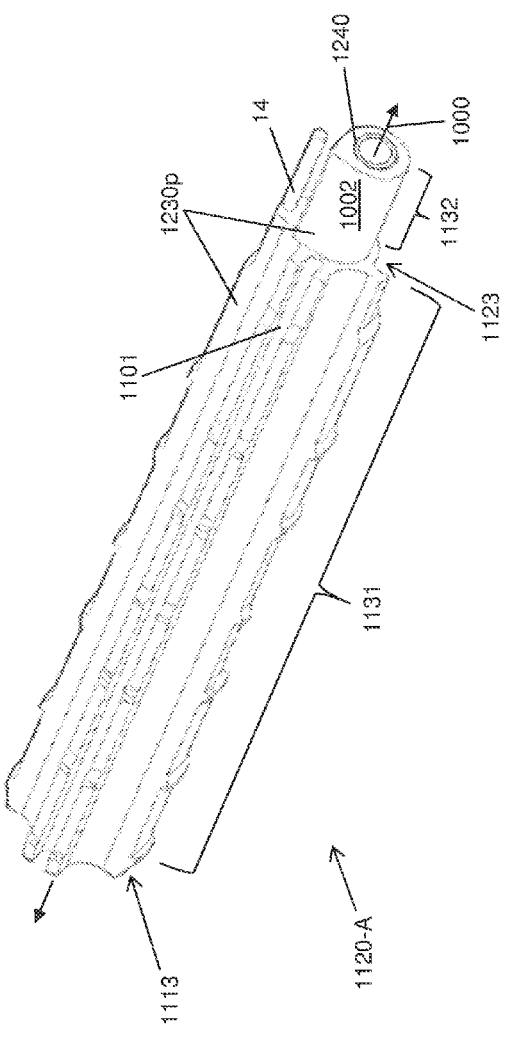
FIG. 11C is a perspective view of a subassembly, according to some alternate embodiments.

FIG. 11C is a perspective view of a subassembly 1120-A, according to some alternate embodiments. Subassembly 1120-A includes core 1240 extending within primary bulk of insulation 1230p, similar to subassembly 1120-P, but does not include terminal connector pin 110, and need not include conductor pin 14. Thus, subassembly 1120-A is employed in a connector assembly for active fixation type A leads, for example, like the lead connector described above, in conjunction with FIG. 6, wherein a proximal portion of an elongate lead conductor (e.g., conductor 600) extends through lumen 1040 of core 1240 to a proximal end thereof, which is coupled to terminal connector pin 110. As described above, this conductor of the active fixation type lead A, which is preferably a coiled conductor, forms a drive shaft with connector pin 110, which may be rotated to extend and retract helix electrode de relative to lead body 130 (FIG. 1), according to constructions and methods known in the art. Since the lead conductor of the active fixation type lead A electrically couples distal-most electrode de to terminal connector pin 110, core 1240 of the corresponding connector assembly need not be part of a circuit like it is in connector assembly 1200 of passive fixation type lead P.

FIG. 12A is a perspective view of the above-described contact circuits, according to some embodiments, wherein the contact circuits are oriented and positioned in relation to one another as they are when integrated into either of subassemblies 1120-P, 1120-A; and FIG. 12B is a perspective view of subassembly 1120-P including the contact circuits. FIG. 12A illustrates each contact circuit including a contact ring 1211, 1212, 1213, which has an outer surface that forms the aforementioned corresponding contact surface cs1, cs2, cs3, and an inner surface to which a corresponding conductor pin proximal end 111, 121, 131 is coupled. Each contact pin 11, 12, 13 is shown including the aforementioned bend 10 between the coupled proximal end 111, 121, 131, and a remainder thereof, to space the remainders inward from the inner surfaces of contact rings 1211, 1212, 1213. Either before or after forming bends 10 in pins 11, 12, 13, each proximal end 111, 121, 131 of the corresponding conductor pin 11, 12, 13, is coupled, for example, by laser welding, to the inner surface of the corresponding ring 1211, 1212, 1213, and then each contact circuit may be assembled together with primary bulk of insulation 1230p as shown in FIG. 12B. It should be noted that the inner surface of each contact ring 1211, 1212, 1213 may be configured so that the coupling of the proximal end 111, 121, 131 of the corresponding pin 11, 12, 13 thereto spaces the remainder of the corresponding pin inward, and each bend 10 is not necessary. FIG. 12A further illustrates each of pins 11, 12 including another bend 1210 formed in proximity to the corresponding distal end 112, 122 thereof, according to some embodiments, to position pin distal ends 112, 122 equidistant from axis 1000, as described above.

Figure 12C:
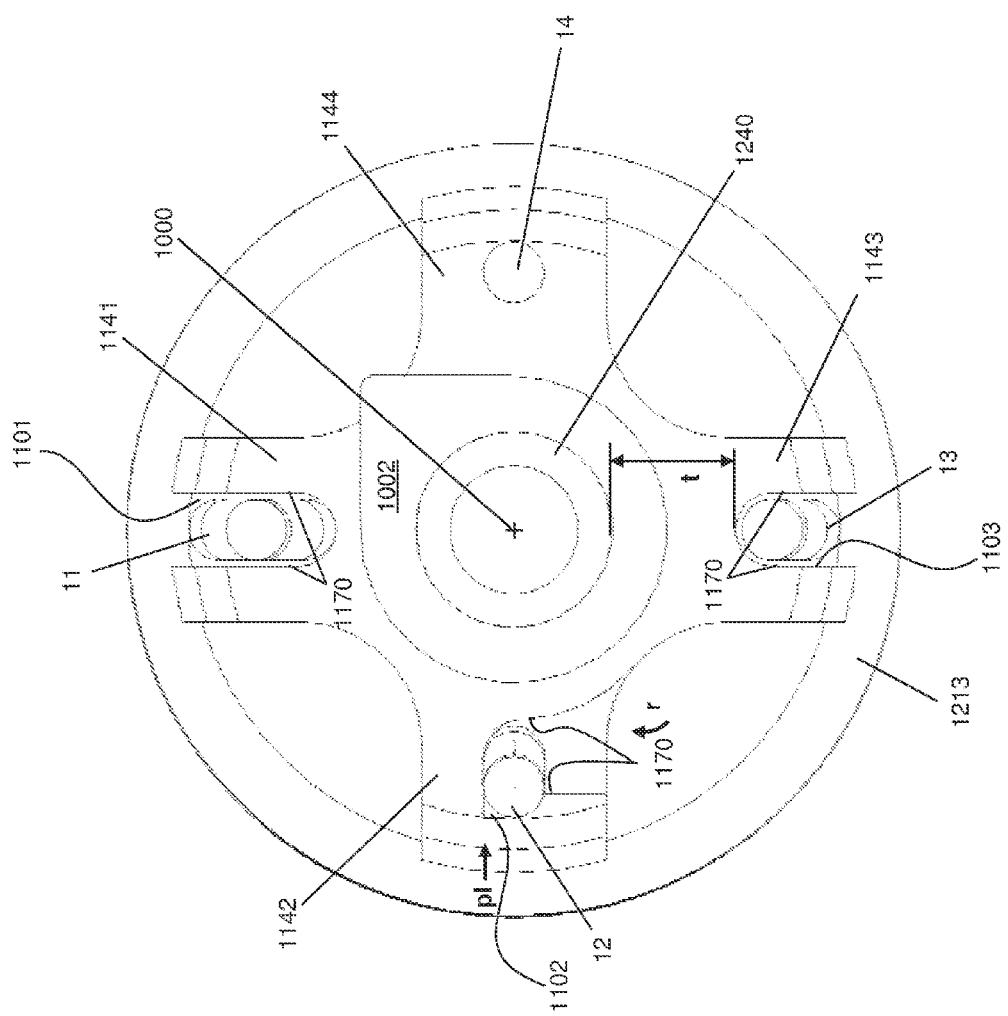
FIG. 12C is an end view of the subassembly shown in FIG. 12B, according to some embodiments.

With reference back to FIG. 11A, circuit-support segment 1131 of primary bulk of insulation 1230p is formed with three open channels 1101, 1102, 1103 configured to receive conductor pins 11, 12, 13 when rings 1211, 1212, 1213 are positioned around circuit-support segment 1131, as shown in FIG. 12B. According to the illustrated embodiment, each channel 1101, 1102, 1103 extends longitudinally within a corresponding cog 1141, 1142, 1143 of primary bulk 1230p; cogs 1141, 1142, 1143 are best seen in the end view of subassembly 1120-P, which is shown in FIG. 12C. FIG. 12C illustrates four cogs 1141, 1142, 1143, 1144 of primary bulk 1230p spaced approximately equidistant from one another around central longitudinal axis 1000, wherein each of conductor pins 11, 12, 13 extends within the corresponding open channel 1101, 1102, 1103, and conductor pin 14 is embedded in cog 1144. With further reference to FIG. 12C, a minimum thickness t of primary bulk 1230p between channels 1101-1103 and core 1240, for example, being approximately 0.010 inch, corresponds to electrical isolation requirements for each pin 11, 12, 13 relative to core 1240. According to some preferred embodiments and methods, primary bulk of insulation 1230p is formed from 75D durometer medical grade polyurethane by injection molding, and a parting line for opposing portions of mold tooling is indicated with an arrow labeled pl in FIG. 12C. Thus, according to the illustrated embodiment, sidewalls 1170 of each open channel 1101-1103, which extend approximately orthogonal to central longitudinal axis 1000, all extend approximately parallel to one another.

With further reference to FIG. 11A, each open channel 1101, 1102, 1103 extends from a distal end 1123 of primary bulk of insulation 1230p to a corresponding pair of outward protruding shoulders 1151, 1152, 1153, which may be formed in all four cogs 1141-1144 to help locate contact rings 12111, 1212, 1213 at a predetermined spacing along circuit support segment 1131. According to some methods, the circuit of ring 1211 coupled to pin 11 is positioned on primary bulk 1230p first, being advanced, with pin 11 located in channel 1101 (FIG. 11C) until ring 1211 is located in between opposing shoulders 1151; then the circuit of ring 1212 coupled to pin 12 is positioned, so that pin 12 is located in channel 1102 and ring 1212 is located between opposing shoulders 1152, and then the circuit of ring 1213 coupled to pin 13 is positioned, so that pin 13 is located in channel 1103 and ring 1213 is located between opposing shoulders 1153. With reference to FIGS. 12B and 12C, to assemble the circuit of ring 1212 and pin 12, pin 12 may be initially aligned along a gap between cogs 1142, 1143 for sliding ring 1212 and pin 12, per arrow s, onto primary bulk 1230p, and then, when ring 1212 is positioned between shoulders 1152, the circuit is rotated, per arrow r, to positioned pin 12 within channel 1102.

Subassembly 1120-P, as shown in FIG. 12B, is positioned within a mold for the injection molding thereabout of secondary bulk of insulation 1230s, which, with reference to FIG. 10, forms sealing surfaces ss1-ss4 and the proximal portion of shank 1232, wherein sealing surfaces ss1-ss4 are formed isodiametric with contact surfaces cs1-cs3 of rings 1211-1213 by the molding operation. With further reference to FIG. 10, flats 1037 are features of second bulk 1230s at which gates of a mold are located, and the molding operation targets diameter D for sealing surfaces ss1-ss4. According to an exemplary embodiment, secondary bulk of insulation 1230s is formed from 75D durometer medical grade polyurethane. A proximal end 1231 of secondary bulk 1230s extends over the above-described junction formed to couple terminal connector pin 110 to conductive core 1240 in subassembly 1120-A, and a distal end of secondary bulk 1230s defines the above-described proximal portion of shank 1232. For those embodiments of connector assemblies and subassemblies that are suitable for active fixation type A leads, and which do not include terminal connector pin 110, an elongate lead conductor (e.g., conductor 600) is inserted through lumen 1040 of conductive core 1240 so that a proximal end thereof is located in proximity to proximal end 1231 of secondary bulk 1230s, where the proximal end of the lead conductor is coupled to terminal connector pin 110, following the molding operation that forms secondary bulk 1230s.

In the foregoing detailed description, the invention has been described with reference to specific embodiments. However, it may be appreciated that various modifications and changes can be made without departing from the scope of the invention as set forth in the appended claims.

The invention claimed is:

1. A connector assembly for an implantable medical electrical lead, the assembly having a central longitudinal axis and a uniform outer diameter conforming to a requirement for the connector to mate with a connector receptacle of an implantable medical device, and the assembly comprising:

a plurality of contact rings extending around the central longitudinal axis and being spaced apart from one another along a length of the assembly, each of the contact rings having an inner surface, and an outer contact surface, each outer contact surface defining the uniform outer diameter;

a bulk of insulation supporting the plurality of contact rings and isolating the contact rings from one another, the bulk of insulation including a plurality of sealing surfaces, and a shank, each sealing surface also defining the uniform outer diameter of the assembly, the shank defining a distal end of the bulk of insulation, and the shank having an asymmetric profile, a first sealing surface of the plurality of sealing surfaces extending from a proximal end of the bulk of insulation to a first ring of the plurality of contact rings, a second sealing surface of the plurality of sealing surfaces extending between the first contact ring and a second contact ring of the plurality of contact rings, and a third sealing surface of the plurality of sealing surfaces extending distally from the second contact ring;

at least one conductor pin extending within the bulk of insulation, a distal end of each conductor pin protruding distally from the bulk of insulation and being exposed alongside the shank thereof, and a proximal end of a first conductor pin of the at least one conductor pin being coupled to the inner surface of the first contact ring; and a core extending within the bulk of insulation, the core being aligned along the central longitudinal axis of the assembly;

wherein the shank of the bulk of insulation includes a proximal portion and a distal portion, the proximal portion being defined by an external groove formed therein, the groove extending around the central longitudinal axis, and the distal portion being defined by the asymmetric profile;

wherein a connector sleeve which isolate the couplings between the connector assembly and a lead body from an environment external to the implantable medical electrical lead, the connector sleeve interlocks with the external groove.

2. The assembly of claim 1, wherein the core includes an outer surface to which a proximal end of a fourth conductor pin of the at least one conductor pin is coupled.

3. The assembly of claim 2, wherein the fourth conductor pin has a bend formed therein, the bend being located between the proximal end of the fourth conductor pin and a remainder thereof such that the remainder is spaced outward from the outer surface of the core.

4. The assembly of claim 2, further comprising a terminal connector pin coupled to the core and protruding proximally from the proximal end of the bulk of insulation.

5. The assembly of claim 1, wherein the at least one conductor pin comprises a plurality of conductor pins, the distal ends of the plurality of conductor pins being spaced apart from one another and spaced approximately equidistant from the central longitudinal axis.

6. The assembly of claim 5, wherein:
the plurality of conductor pins includes the first conductor pin, a second conductor pin, and a third conductor pin; and
the plurality of contact rings includes the first and second contact rings and a third contact ring, a proximal end of the second conductor pin being coupled to the inner surface of the second contact ring, and a proximal end of the third conductor pin being coupled to the inner surface of the third contact ring.

7. The assembly of claim 6, wherein the core includes an outer surface to which a proximal end of a fourth conductor pin of the plurality of conductor pins is coupled.

8. The assembly of claim 5, further comprising:
a transition fitting joined to the shank of the bulk of insulation, the fitting comprising a lumen, and at least two peripheral grooves, the lumen being sized to receive an inner portion of a body of the lead; and
wherein each groove of the transition fitting supports the distal end of a corresponding conductor pin of the plurality of conductor pins; and
each groove of the transition fitting is sized to receive a corresponding conductor of a plurality of conductors of the body of the lead, such that each conductor pin of the assembly can be coupled to the corresponding lead conductor within the corresponding groove, when the inner portion of the lead body is received in the lumen of the fitting.

9. The assembly of claim 8, wherein the transition fitting further comprises a strain relief portion extending distally from the grooves, the lumen of the fitting extending within the strain relief portion, and the strain relief portion being sized to fit between the inner portion of the lead body and the plurality of conductors of the lead body, when the inner portion is received in the lumen of the fitting, and each conductor of the plurality of conductors is received in the corresponding groove of the fitting.

10. The assembly of claim 8, wherein:
the transition fitting further comprises a strain relief portion extending distally from the grooves, the strain relief portion including a plurality of longitudinal slots, each slot aligned with a corresponding groove and extending therefrom to an open end at a distal end of the fitting;
the lumen of the fitting extends within the strain relief portion; and
the strain relief portion is sized to fit around the inner portion of the lead body, the plurality of conductors of the lead body, and an outer insulation layer of the lead body, which overlays the plurality of conductors, when the inner portion is received in the lumen, and each conductor of the plurality of conductors is received in the corresponding groove, via the corresponding slot.

11. A subassembly for a connector assembly of an implantable medical electrical lead, the subassembly comprising:
a bulk of insulation including a circuit-support segment and a shank segment, the circuit-support segment extending along a length of a central longitudinal axis of the subassembly, from a proximal end of the circuit-support segment to a distal end of the circuit-support segment, the shank segment extending distally, along the central longitudinal axis, from the distal end of the circuit-support segment, and the circuit-support segment including three longitudinally-extending open channels;
a core extending within the bulk of insulation, the core being aligned along the central longitudinal axis of the assembly;
a plurality of contact rings mounted around the circuit-support segment of the bulk of insulation and spaced apart from one another along the length thereof, an outer contact surface of each of the plurality of contact rings defining a uniform outer diameter, the uniform outer diameter conforming to a requirement of the connector assembly to mate with a connector receptacle of an implantable medical device;
a first conductor pin extending within a first channel of the three open channels of the circuit-support segment of the bulk of insulation, a proximal end of the first conductor pin being coupled to an inner surface of a first contact ring of the plurality of contact rings, and a distal end of the first conductor pin being exposed alongside the shank segment of the bulk of insulation;
a fourth conductor pin extending within the bulk of insulation, the fourth conductor pin including a proximal end coupled to an outer surface of the core, within the bulk of insulation, and a distal end protruding from the distal end of the circuit-support segment of the bulk of insulation, the distal end of the fourth conductor pin being exposed alongside the shank segment of the bulk of insulation; and
a terminal connector pin coupled to a proximal end of the core in proximity to the proximal end of the circuit-support segment of the bulk of insulation.

12. The subassembly of claim 11, wherein the shank segment of the bulk of insulation has an asymmetric profile.

13. The subassembly of claim 11, further comprising a second conductor pin, the second conductor pin extending within a second channel of the three open channels of the circuit-support segment of the bulk of insulation, a proximal end of the second conductor pin being coupled to an inner surface of a second contact ring of the plurality of contact rings, and a distal end of the second conductor pin being exposed alongside the shank segment of the bulk of insulation.

14. The subassembly of claim 13, further comprising a third conductor pin, the third conductor pin extending within a third channel of the three open channels of the circuit-support segment of the bulk of insulation, a proximal end of the third conductor pin being coupled to an inner surface of a third contact ring of the plurality of contact rings, and a distal end of the third conductor pin being exposed alongside the shank segment of the bulk of insulation.

15. The subassembly of claim 14, wherein the distal ends of the first, second and third conductor pins are spaced apart from one another and spaced approximately equidistant from the central longitudinal axis.

16. The subassembly of claim 14, further comprising:
   a fourth conductor pin extending within the bulk of insulation, the fourth conductor pin including a proximal end coupled to an outer surface of the core, within the bulk of insulation, and a distal end protruding from the distal end of the circuit-support segment of the bulk of insulation, the distal end of the fourth conductor pin being exposed alongside the shank segment of the bulk of insulation; and
   a terminal connector pin coupled to a proximal end of the core in proximity to the proximal end of the circuit-support segment of the bulk of insulation.

17. The subassembly of claim 16, wherein the distal ends of the first, second, third and fourth conductor pins are spaced apart from one another and spaced approximately equidistant from the central longitudinal axis.

* * * * *